(12) United States Patent
Ojima

(10) Patent No.: US 7,981,926 B2
(45) Date of Patent: Jul. 19, 2011

(54) FLUOROTAXOIDS

(75) Inventor: Iwao Ojima, Port Jefferson, NY (US)

(73) Assignee: Research Foundation of State University of New York, Albany, NY (US)

( * ) Notice: Subject to any disclaimer, the term of this patent is extended or adjusted under 35 U.S.C. 154(b) by 695 days.

(21) Appl. No.: 11/990,323

(22) PCT Filed: Aug. 11, 2006

(86) PCT No.: PCT/US2006/031413
§ 371 (c)(1),
(2), (4) Date: Jun. 23, 2008

(87) PCT Pub. No.: WO2007/021957
PCT Pub. Date: Feb. 22, 2007

(65) Prior Publication Data
US 2009/0118355 A1    May 7, 2009

Related U.S. Application Data

(60) Provisional application No. 60/707,665, filed on Aug. 12, 2005.

(51) Int. Cl.
*C07D 305/14* (2006.01)
*A61K 31/337* (2006.01)
(52) U.S. Cl. .................. 514/449; 549/510; 549/511
(58) Field of Classification Search .................. 549/510, 549/511; 514/449
See application file for complete search history.

(56) References Cited

U.S. PATENT DOCUMENTS

| | | | |
|---|---|---|---|
| 6,096,909 A | 8/2000 | Ojima |
| 6,100,411 A | 8/2000 | Ojima |
| 6,458,976 B1 | 10/2002 | Ojima |
| 6,500,858 B2 | 12/2002 | Ojima |
| 6,835,746 B2 | 12/2004 | Ojima |

FOREIGN PATENT DOCUMENTS

WO  PCT/US2004/036027   5/2005
WO  PCT/US2005/004715   9/2005

*Primary Examiner* — Janet L. Andres
*Assistant Examiner* — Raymond Covington
(74) *Attorney, Agent, or Firm* — Hoffmann & Baron, LLP

(57) ABSTRACT

The invention relates to fluorinated second generation taxoid compounds, pharmaceutical formulations thereof, and their use for inhibiting the growth of cancer cells in a mammal.

11 Claims, No Drawings

FLUOROTAXOIDS

The present application claims priority to U.S. Provisional Application No. 60/707,665 filed on Aug. 12, 2005, which application is incorporated herein by reference in its entirety.

The present invention was made with government support under Grant No. R01 GM 42798 awarded by the National Institute of General Medical Sciences and Grant No. R01 CA10331 awarded by the National Cancer Institute. The United States government has certain rights in this invention.

BACKGROUND OF THE INVENTION

First generation taxoid compounds such as paclitaxel (Taxol®) and docetaxel (Taxotere®) have gained prominence as some of the most efficacious anticancer drugs. See E. K. Rowinsky, Annual Review of Medicine 1997, 48, 353; M. Suffness, Taxol Science and Applications; CRC Press: New York, 1995.

Second generation taxoid compounds with orders of magnitude higher potency have also been developed. See U.S. Pat. Nos. 6,096,909, 6,100,411, 6,458,976, and 6,500,858 to I. Ojima; G. I. Georg, T. Chen, I. Ojima, and D. M. Vyas (Eds.), "Taxane Anticancer Agents: Basic Science and Current Status," ACS Symp. Series 583; American Chemical Society, Washington, D.C., 1995); I. Ojima, et al, Bioorg. Med. Chem. Lett., 1999, 9, 3423-3428; I. Ojima, et al, J. Med. Chem., 1996, 39, 3889-3896; and I. Ojima, G. D. Vite, K.-H. Altmann (Eds.), "Anticancer Agents: Frontiers in Cancer Chemotherapy," ACS Symp. Series 796, American Chemical Society, Washington, D.C., 2001.

While these and other second generation taxoids have shown a high degree of efficacy in the treatment of various forms of cancer, there is a continuing need for improving the activity, metabolic stability, and mode of action of these compounds. There is a particular need to improve the efficacy of second generation taxoid compounds against multi-drug resistance (MDR) in the treatment of cancer. There is also a need for new taxoid compounds having less acute side effects and higher metabolic stability.

SUMMARY OF THE INVENTION

These, and other objectives as will be apparent to those of ordinary skill in the art, have been achieved by providing a compound having the formula:

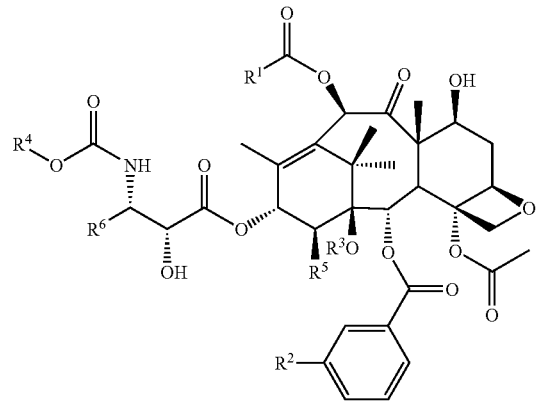

(1)

wherein:
$R^1$ represents an alkyl, alkenyl, alkylamino, dialkylamino, or alkoxy group having one to six carbon atoms; a non-aromatic carbocyclic alkyl or alkenyl group having three to seventeen ring carbon atoms; a carbocyclic aryl group having six to eighteen ring carbon atoms; a non-aromatic heterocyclic group having three to seventeen ring carbon atoms or a heterocyclic aryl group having five to seventeen ring carbon atoms, wherein said cyclic groups can be unfused or fused, and unsubstituted or substituted;

$R^2$ represents a hydrogen; alkyl, alkenyl, alkoxy, alkenyloxy, acyloxy, alkylthio, alkenylthio, alkylamino or dialkylamino having one to six carbon atoms; halogen; fluoroalkyl group having one to three fluorine atoms and one to three carbon atoms; hydroxyl; carboxyl; amino or azido; $R^3$ and $R^5$ both represent hydrogen, or $R^3$ and $R^5$ are linked as a cyclic carbonate;

$R^4$ represents an alkyl or alkenyl group having one to six carbon atoms; or a cycloalkyl or cycloalkenyl group having three to seven ring carbon atoms; and $R^6$ represents a fluorovinyl, difluorovinyl, or trifluorovinyl group having the formula

(2)

wherein $R^7$, $R^8$, and $R^9$ each independently represent a hydrogen or fluoro group, provided that at least one of $R^7$, $R^8$, and $R^9$ represents a fluoro group.

In another embodiment, the invention provides a pharmaceutical composition comprising the fluorotaxoid composition.

The invention is further directed to a method for inhibiting the growth of cancer cells in a mammal in need thereof, the method comprising administering to the mammal an effective amount of the fluorotaxoid compound described above.

DETAILED DESCRIPTION OF THE INVENTION

In one aspect, the invention relates to second generation fluorotaxoid compounds. The fluorotaxoid compounds contain a fluorovinyl, difluorovinyl, or trifluorovinyl group at the C3' position of a second generation taxoid compound.

In a preferred embodiment, the taxoid compounds of the invention are represented by the formula:

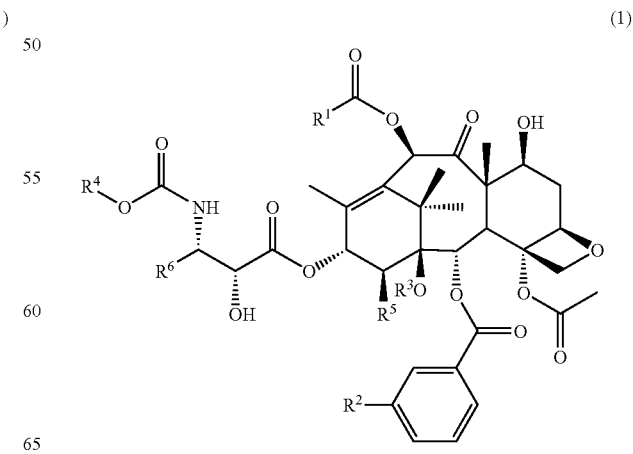

(1)

In formula (1), $R^1$ represents a hydrocarbon group selected from an alkyl, alkenyl, alkylamino, dialkylamino, or alkoxy group having one to six carbon atoms; a non-aromatic carbocyclic alkyl or alkenyl group having three to seventeen ring carbon atoms; an aryl group having six to eighteen ring carbon atoms; or a non-aromatic heterocyclic group having three to seventeen ring carbon atoms; or a heteroaryl group having five to seventeen ring carbon atoms. These acyclic and cyclic hydrocarbon groups may be attached to the fluorotaxoid at any carbon position.

Some examples of suitable straight-chained alkyl groups include methyl, ethyl, n-propyl, n-butyl, n-pentyl, and n-hexyl.

Some examples of suitable branched alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, and 4-methylpentyl.

Some examples of suitable straight-chained alkenyl groups include vinyl, 2-propen-1-yl, 2-buten-1-yl, 3-buten-1-yl, 2-penten-1-yl, 3-penten-1-yl, 1,3-pentadien-1-yl, 4-penten-1-yl, 2-hexen-1-yl, 3-hexenyl, 4-hexen-1-yl, and 5-hexen-1-yl.

Some examples of suitable branched alkenyl groups include propen-2-yl, 1-buten-2-yl, 2-buten-2-yl, 1-buten-3-yl, 1-penten-2-yl, 1-penten-3-yl, 1-penten-4-yl, 2-penten-2-yl, 2-penten-3-yl, 2-penten-4-yl, 1-buten-3-methyl-2-yl, 1-buten-3-methyl-3-yl, 2-buten-2-methyl-1-yl, 2-buten-2-methyl-3-yl, 2-buten-2-methyl-4-yl, 2-buten-2-methylenyl, 2-buten-2,3-dimethyl-1-yl, 1-hexen-2-yl, 1-hexen-3-yl, 1-hexen-4-yl, 1-hexen-5-yl, 2-hexen-3-yl, 2-hexen-4-yl, 2-hexen-5-yl, 3-hexen-2-yl, 3-hexen-3-yl, 1-penten-3-methyl-2-yl, 1-penten-3-methyl-3-yl, 1-penten-3-methyl-4-yl, 2-penten-3-methyl-2-yl, and 2-penten-3-methyl-4-yl.

Some examples of suitable alkylamino groups include methylamino, ethylamino, n-propylamino, iso-propylamino, n-butylamino, sec-butylamino, iso-butylamino, tert-butylamino, n-pentylamino, iso-pentylamino, neo-pentylamino, n-hexylamino, 2,3-dimethylbutylamino, cyclopropylamino, cyclobutylamino, cyclopentylamino, cyclohexylamino, cycloheptylamino, 2-hydroxyethylamino, 2-(2-hydroxyethyleneoxy)-ethylamino, 2-methoxyethylamino, 2-ethoxyethylamino, and 3-hydroxypropylamino.

Some examples of suitable dialkylamino groups include dimethylamino, methylethylamino, methyl(n-propyl)amino, methyl(iso-propylamino), methyl(n-butyl)amino, methyl(iso-butyl)amino, methyl(n-pentyl)amino, methyl(iso-pentyl)amino, methyl(neopentyl)amino, diethylamino, ethyl(n-propyl)amino, ethyl(iso-propylamino), ethyl(n-butyl)amino, ethyl(iso-butyl)amino, di(n-propyl)amino, and di(iso-propyl)amino.

Some examples of suitable alkoxy groups include methoxy, ethoxy, n-propoxy, iso-propoxy, n-butoxy, iso-butoxy, sec-butoxy, tert-butoxy, n-pentoxy, 1-methylbutoxy, 2-methylbutoxy, 3-methylbutoxy, n-hexoxy, 1,1-dimethylbutoxy, 1,2-dimethylbutoxy, 2,2-dimethylbutoxy, 2,3-dimethylbutoxy, 1-ethylbutoxy, 2-ethylbutoxy, cyclopropyloxy, cyclobutyloxy, 2,4-dimethylcyclobutyloxy, cyclohexyloxy, cyclopropylmethyloxy, cyclohexylmethyloxy, and phenoxy.

The non-aromatic carboxylic alkyl or alkenyl groups of $R^1$ have three to seventeen ring carbon atoms. Some examples of suitable non-aromatic carboxylic alkyl groups include cyclopropyl, cyclobutyl, cyclopentyl, cyclohexyl, and cycloheptyl. Some examples of suitable non-aromatic carboxylic alkenyl groups include cyclobutenyl, cyclobutadienyl, cyclopentenyl, cyclohexenyl, cyclohexadienyl, cycloheptenyl, and cycloheptadienyl.

The cyclic groups described above can be fused or unfused. The total number of carbon atoms include carbon atoms from fused rings.

A preferred unfused carbocyclic aryl group is phenyl. Some examples of suitable fused aryl groups include naphthyl, phenanthryl, anthracenyl, triphenylenyl, chrysenyl, and pyrenyl.

The heterocyclic aryl groups have five to seventeen atoms in the ring with one or more heteroatoms, preferably nitrogen, sulfur, or oxygen atoms. Some examples of suitable heteroaryl groups include pyridinyl, pyrimidinyl, triazinyl, imidazolyl, benzimidazolyl, pyrrolyl, cinnolinyl, phthalazinyl, quinazolinyl, purinyl, 2,6-naphthyridinyl, 1,8-naphthyridinyl, quinolinyl, isoquinolinyl, carbazolyl, oxazolyl, thiophenyl, thiazolyl, furyl, pyridazinyl, pyrazolyl, 1,4-diazanaphthalenyl, indolyl, pyrazinyl, 4,5-diazaphenanthrene, and benzoxazole.

$R^1$ can also be a non-aromatic heterocyclic group. Some examples of suitable non-aromatic heterocyclic groups include piperidinyl, piperidinyl-N-oxide, N-methylpiperidinyl, piperazinyl, 1-methylpiperazinyl, piperazinyl-N-oxide, 1-acetylpiperazinyl, 1-(o-tolyl)piperazinyl, homopiperazinyl, and morpholino.

The cycloalkyl, cycloalkenyl, aryl, heteroaryl and non-aromatic heterocyclic rings described above for $R^1$ can be substituted with any of the hydrocarbon groups thus far described.

Some examples of hydrocarbyl-substituted cycloalkyl groups include 2-methylcyclopropyl, 2-ethylcyclopropyl, 2-methylcyclobutyl, 3-methylcyclobutyl, 2-methylcyclopentyl, 2,3-dimethylcyclopentyl, 3-iso-propylcyclopentyl, 2,6-dimethylcyclohexyl, 4-(t-butyl)cyclohexyl, 2-vinylcyclohexyl, 3-allylcyclopentyl, 3,4-diallylcyclopentyl, 1-(4-pyridinyl)piperidinyl, 1-(4-pyridinylmethyl)piperidinyl, 4-(4-pyridinyl)piperidinyl, 4-(4-pyridinyl)piperazin-1-yl, and bicyclohexyl groups.

Some examples of hydrocarbyl-substituted cycloalkenyl groups include 3-methyl-3-cyclopenten-1-yl, 3,4-dimethyl-3-cyclopenten-1-yl, 2-iso-propyl-2-cyclopenten-1-yl, 2,3-diethyl-2-cyclopenten-1-yl, 4-vinyl-1-cyclohexen-1-yl, 3,4-diethyl-3-cyclopenten-1-yl, and 3,4-diallyl-3-cyclopenten-1-yl groups.

Some examples of hydrocarbyl-substituted aryl groups include tolyl, mesityl, xylyl, cumenyl, cymenyl, 3,5-di(t-butyl)phenyl, 2-methylnaphthyl, 2-vinylphenyl, 2-vinylbenzyl, 2-vinylnaphthyl, 4-cyclohexylphenyl, biphenyl, 4-(4-piperidinyl)pyridinyl, and p-terphenyl groups.

Some examples of hydrocarbyl-substituted heteroaryl groups include 2-methylpyridin-1-yl, 2-ethylpyridin-1-yl, 3-vinylimidazol-1-yl, 2-methylimidazol-1-yl, 2-methylquinoxalin-1-yl, 1-allylbenzotriazolyl, 2,2'-bipyridyl, 4,4'-bipyridyl, 4-methylpyrazinyl, 4-(pyridinylmethyl)-pyridinyl, 4-benzylpyrazinyl, nicotinamidyl, 2-methylfuranyl, 5-methylfurfurylamino, 2-methylthiopheneyl, 4-methyloxazolyl, 2,5-diphenyl-4-methyloxazolyl, and 4-methylthiazolyl groups.

Alternatively, the cycloalkyl, cycloalkenyl, aryl, heteroaryl and non-aromatic heterocyclic rings described above for $R^1$ can be substituted with a halogen, nitro, hydroxyl carboxyl, amino or azido group.

In formula (1), $R^2$ can also represent any of the hydrocarbon groups described above with regard to $R^1$. For example, $R^2$ can represent alkyl, such as methyl; alkenyl; alkoxy, such as methoxy; alkenyloxy; acyloxy; alkylthio; alkenylthio;

alkylamino; or dialkylamino having one to six carbon atoms. Preferably, the hydrocarbon group contains a maximum of two carbon atoms. Alternatively, $R^2$ can also represent hydrogen; a halogen, such as iodo, bromo, chloro or fluoro; or fluoroalkyl having one to three fluorine atoms and one to three carbon atoms, for example, trichloromethyl; hydroxyl; amino; carboxyl; or azido.

$R^3$ and $R^5$ both preferably represent hydrogen, or $R^3$ and $R^5$ together represent a cyclic carbonate (i.e., —O—C(=O)—O—).

$R^4$ represents any of the alkyl, alkenyl, cycloalkyl, or cycloalkenyl groups described above for $R^1$. Preferably, $R^4$ is a tert-butyl group.

In formula (1), $R^6$ represents a fluorinated vinyl group having the formula

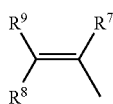

(2)

In formula (2), $R^7$, $R^8$, and $R^9$ each independently represent a hydrogen or fluoro group provided that at least one of $R^7$, $R^8$, and $R^9$ represents a fluoro group. The fluorinated vinyl group can be a fluorovinyl, difluorovinyl, or trifluorovinyl group.

The fluorovinyl group can be a 2-fluorovinyl group (—CH=CHF) or a 2-fluorovinyl group (—CF=CH$_2$). In addition, the 2-fluorovinyl group can be in a cis- or trans-configuration.

The difluorovinyl group can be a 2,2-difluorovinyl group (—CH=CF$_2$) or a 1,2-difluorovinyl group (—CF=CHF). The 1,2-difluorovinyl group can have the fluoro substituents in either a cis- or trans-configuration with respect to each other.

The trifluorovinyl group corresponds to a 1,2,2-trifluorovinyl group (—CF=CF$_2$).

In a preferred embodiment, the taxoid compounds of the present invention are represented by the formula:

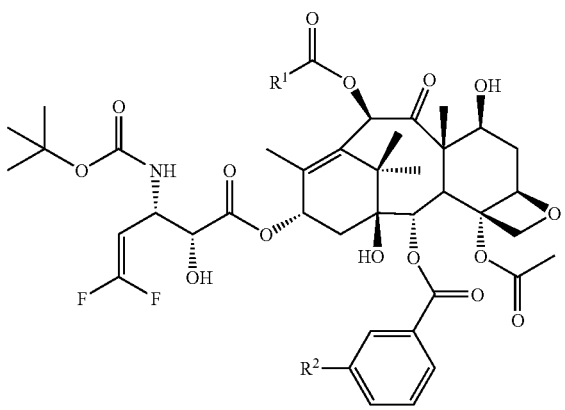

(3)

In formula (3), $R^1$ and $R^2$ are independently as described above. For example, $R^1$ can be methyl, ethyl, methoxy, dimethylamino or cyclopropyl and $R^2$ can be hydrogen, methyl, methoxy, chloro, fluoro or azido. More preferably, $R^1$ represents methyl, ethyl, methoxy, or cyclopropyl, and $R^2$ represents hydrogen, methoxy, or azido.

Some particularly preferred taxoid compounds of the present invention include those listed in the table below. These taxoids have shown particular potency for the inhibition of the growth of cancer cells as shown in the following table. The results were obtained according to the methods of Skehan et al (See Skehan et al., J. Nat. Cancer Inst., 82, 1107 (1990)), as more fully described in the Examples. The resistance factor (R/S) shown in the table is a measure of the degree of resistance of a cell line against a taxoid compound. The resistance factor is a ratio of the cytoxicity of a taxoid compound against a drug-resistant cell line (R) as compared to its cytoxicity against a drug-sensitive cell line (S).

Highly Potent Difluorovinyl-taxoids (IC$_{50}$ nM)

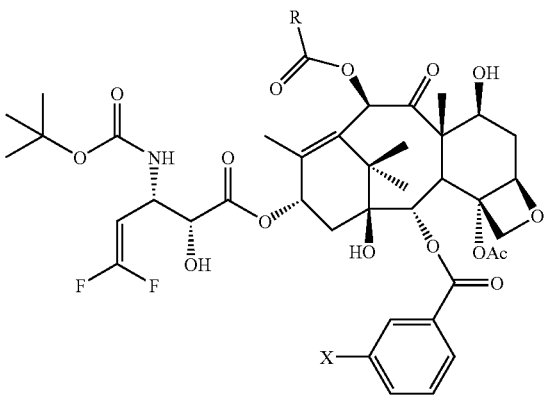

| Taxoid | R | X | MCF7 (breast) | MCF7-R (breast) | R/S |
|---|---|---|---|---|---|
| Paclitaxel | Me | H | 1.2 | 300 | 250 |
| SB-T-12851 | Me | H | 0.099 | 0.95 | 9.6 |
| SB-T-12852-1 | cyclo-Pr | MeO | 0.092 | 0.48 | 5.2 |
| SB-T-12853-1 | Et | MeO | 0.34 | 0.57 | 1.7 |
| SB-T-12855-1 | MeO | MeO | 0.078 | 0.50 | 6.4 |
| SB-T-12851-3 | Me | N$_3$ | 0.092 | 0.34 | 3.7 |
| SB-T-12852-3 | cyclo-Pr | N$_3$ | 0.092 | 0.45 | 4.9 |
| SB-T-12855-3 | MeO | N$_3$ | 0.076 | 0.40 | 5.3 |

The fluorotaxoid compounds are either uncharged or in the form of pharmaceutically acceptable salts. The term "pharmaceutically acceptable salt" refers to a salt prepared from a suitable compound and, for example, an acid or a base. The salt is acceptably non-toxic and has acceptable pharmacokinetics. Such salts are formed by well known procedures.

Suitable acids for producing salts of the compounds of the invention include mineral acids and organic acids. Some examples of mineral acids include hydrochloric, hydriodic, hydrobromic, phosphoric, metaphosphoric, nitric and sulfuric acids. Some examples of organic acids include tartaric, acetic, citric, maleic, malic, benzoic, glycollic, gluconic, gulonic, succinic, arenesulfonic, e.g. p-toluenesulfonic acids, and the like.

Suitable bases for producing salts of the compounds of the invention include inorganic bases and organic bases. Some examples of inorganic bases include ammonia and the hydroxides of lithium, sodium, potassium, magnesium and calcium. Some examples of organic bases include primary, secondary, and tertiary alkyl amines.

In another aspect, the invention is directed to a pharmaceutical composition comprising a compound according to formula (1) or formula (3) and a pharmaceutically acceptable carrier. Compositions may, for example, be pills, capsules, solutions, creams, etc.

In this specification, a pharmaceutically acceptable carrier is considered to be synonymous with a vehicle or an excipient as understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical formulation may also include one or more of the following: a stabilizer, a surfactant, preferably a nonionic surfactant, and optionally a salt and/or a buffering agent.

The stabilizer can be, for example, an amino acid, e.g., glycine; or an oligosaccharide, e.g., sucrose, tetralose, lactose or a dextran. Alternatively, the stabilizer may be a sugar alcohol, e.g., mannitol; or a combination thereof.

The surfactant may be, for example, an ionic surfactant, such as a polyacrylate. Alternatively, the surfactant may be a nonionic surfactant, such as a polyethylene glycol, polyoxyethylene polyoxypropylene glycol, or polysorbate. Some examples of such non-ionic surfactants include Tween 20, Tween 80, and Pluronic F-68 at from about 0.001% (w/v) to about 10% (w/v).

The salt or buffering agent may be any salt or buffering agent, such as, for example, sodium chloride, sodium or potassium phosphates, citric acid, sodium or potassium citrates, or a mixture thereof. The buffering agent is useful for maintaining the pH of the compounds of the invention. The salt and/or buffering agent is also useful to maintain the osmolality at a level suitable for administration to a mammal. For example, the salt or buffering agent can be present at a roughly isotonic concentration of about 150 mM to about 300 mM.

The pharmaceutical compositions of the inventions may additionally contain one or more conventional additives. Some examples of such additives include a solubilizer, such as, for example, glycerol; an antioxidant such as, for example, benzalkonium chloride (a mixture of quaternary ammonium compounds, known as "quart"), benzyl alcohol, chloretone or chlorobutanol; an anaesthetic agent such as, for example, a morphine derivative; or an isotonic agent, etc. As a further precaution against oxidation or other spoilage, the compounds of the inventions may be stored under nitrogen gas in vials sealed with impermeable stoppers.

When aqueous suspensions are used for oral administration, emulsifying and/or suspending agents are commonly added. In addition, coloring, sweetening and/or flavoring agents may be added to the oral compositions.

Pharmaceutical compositions are preferably sterile. The pH of the solutions can be suitably adjusted and buffered. For intravenous use, the total concentration of the solute(s) can be controlled in order to render the preparation isotonic.

Carrier compositions deemed to be suited for topical use include gels, salves, lotions, creams, ointments and the like. The compounds can also be incorporated with a support base or matrix or the like which can be directly applied to skin.

In another aspect, the invention is directed to inhibiting the growth of cancer cells in a mammal in need thereof. In the method, an effective amount of a fluorotaxoid compound of the invention is administered to a mammal.

The cancer cells can be any type of cancer treatable by the taxoid compounds. For example, the cancer can be breast, ovary, lung, head, neck, colon, pancreatic, melanoma, brain, prostate, or renal cancer.

Any mammal in need thereof can be treated in accordance with the present invention. Mammals include, for example, humans, baboons, and other primates, as well as pet animals such as dogs and cats, laboratory animals such as rats and mice, and farm animals such as horses, sheep, and cows.

The method of the invention comprises administering an effective amount of a fluorotaxoid compound. An effective amount of the fluorotaxoid is any amount effective in treating cancer or for inhibiting the growth of cancer cells in a mammal in need thereof.

The actual administered amount of the fluorotaxoid compound will vary according to various factors well known in the art, e.g., the type of cancer, the particular fluorotaxoid being administered, the mode of administration, and the particular subject being treated. The amount required for effective treatment is governed by pharmacological standards and by the discretion of medical practitioners in the art. For example, the effective amount can be determined during clinical and pre-clinical trials by methods familiar to physicians and clinicians.

The minimum amount of a fluorotaxoid administered to a human is the lowest amount capable of inhibiting the growth of cancer cells. The maximum amount is the highest effective amount that does not cause undesirable or intolerable side effects. The minimum amount can be, for example, 0.01, 0.05, or 0.1 milligrams per kilogram body weight per day. The maximum amount can be, for example, 10, 50, or 100 milligrams per kilogram body weight per day. Higher doses may be employed to treat the cancer to the extent patient tolerance permits.

The fluorotaxoid formulation may be administered alone or as an adjunct with other conventional drugs for treating cancer. The adjunctive drugs can be, for example, chemotherapy drugs. Some examples of chemotherapy drugs include methotrexate (Abitrexate®), fluorouracil (Adrucil®), hydroxyurea (Hydrea®), and mercaptopurine (Purinethol®).

The fluorotaxoid formulation may be administered by any suitable method known in the art. Some examples of suitable modes of administration include oral, systemic, and topical administration.

For oral administration, liquid or solid oral formulations can be used, as known in the art. Some examples of formulations suitable for oral administration include tablets, capsules, pills, troches, elixirs, suspensions, and syrups.

Systemic administration includes enteral or parenteral modes of administration, e.g., intravenous; intramuscular; subcutaneous; or intraperitoneal modes of administration. For example, the fluorotaxoid formulation may be administered by injection of a solution or suspension; or intranasally, in the form of, for example, a nebulizer, liquid mist, or intranasal spray; or transdermally, in the form of, for example, a patch; or rectally, in the form of, for example, a suppository; or intrabronchially, in the form of, for example, an inhaler spray.

Suitable carrier compositions for topical use include gels, salves, lotions, creams, ointments, and the like. The compounds can also be incorporated with a support base or matrix or the like which can be directly applied to skin.

The timing of the administration of the fluorotaxoid formulation may also be modified. For example, the formulation may be administered intermittently or by controlled release. Controlled release administration is a method of drug delivery to achieve a certain level of the drug over a particular period of time. See, for example, U.S. Patent Publication No. 2004/0115261, incorporated herein by reference.

Examples have been set forth below for the purpose of illustration and to describe the best mode of the invention at the present time. However, the scope of this invention is not to be in any way limited by the examples set forth herein.

EXAMPLES

Example 1

Synthesis of 4-difluorovinyl β-lactam (3R,4S)-3-AcO-β-lactam was prepared through [2+2] ketene-imine cycloaddition, followed by enzymatic optical resolution of racemic β-lactam (Scheme III-20).

Scheme III-20. Synthesis of (3R,4S)-3-AcO-β-lactam

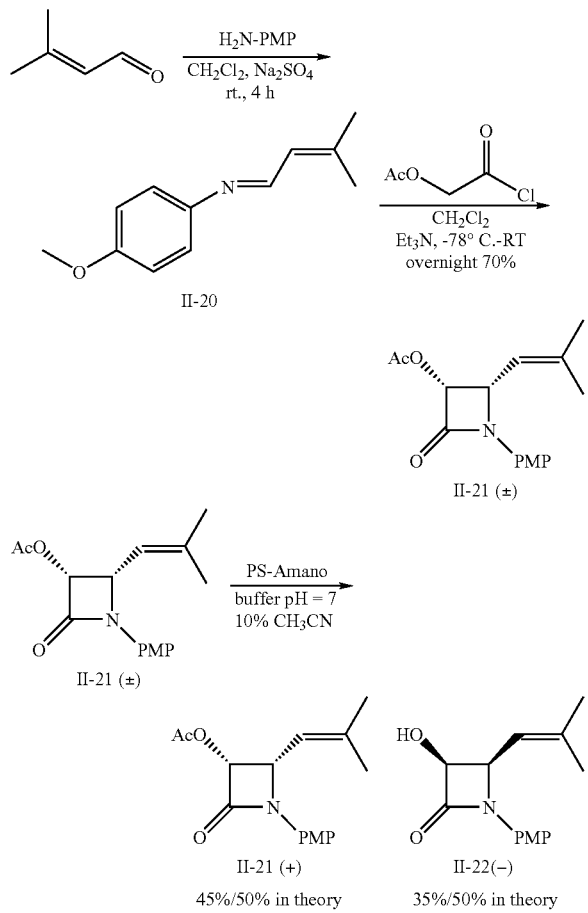

The protecting group of the 3-acetoxy moiety of (3R,4S)-3-AcO-β-lactam was changed to triisopropylsilyl (TIPS). The resulting (3R,4S)-1-PMP-3-TIPSO-4-(2-methyl-1-propenyl)azetidin-2-one II-(+) was subjected to ozonolysis to give (3R,4S)-1-PMP-3-TIPSO-4-formylazetidin-2-one III-47 (Scheme III-21).

Scheme III-21. Synthesis of (3R,4S)-1-PMP-3-TIPSO-4-formylazetidin-2-one

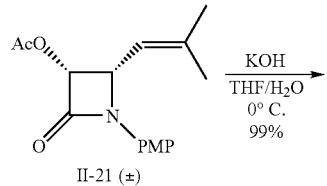

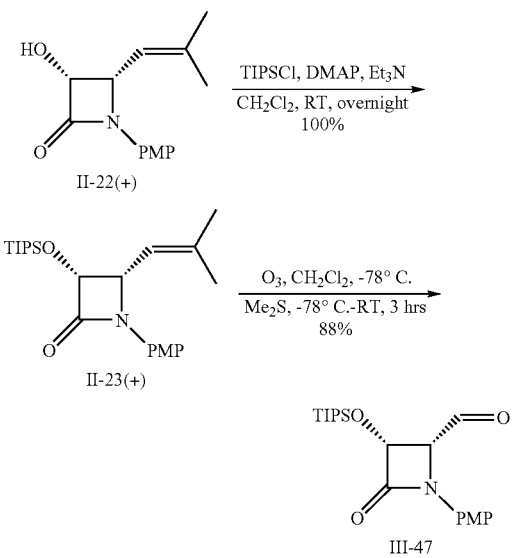

Enantiopure (3R,4S)-1-PMP-3-TIPSO-4-formylazetidin-2-one III-47 was transformed to (3R,4S)-1-PMP-3-TIPSO-4-difluorovinyl-2-one III-48 using $CBr_2F_2$, hexamethylphosphorous triamide (HMPA), and Zn in THF (Scheme III-22).

Scheme III-22. Synthesis of (3R,4S)-1-PMP-3-TIPSO-4-difluorovinyl-2-one

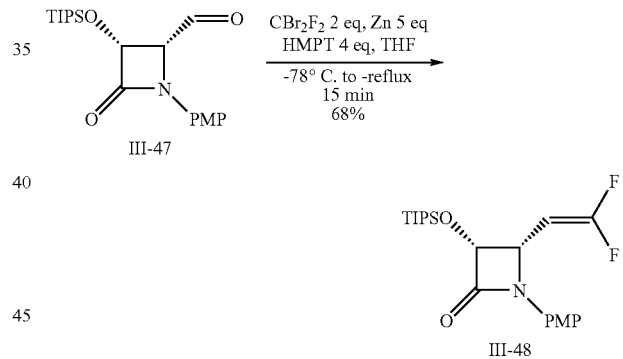

Finally the PMP group was removed using cerium ammonium nitrate (CAN) to give enantiopure (3R,4S)-3-TIPSO-4-difluorovinylazetidin-2-one III-49(+) followed by carbalkoxylation with di-t-butyl dicarbonate ($Boc_2O$) to give desired (3R,4S)—N-Boc-3-TIPSO-4-difluorovinylazetidin-2-one III-50 in excellent yields (Scheme III-24).

Scheme III-24. Synthesis of (3R,4S)-N-Boc-3-TIPSO-4-difluorovinylazetidin-2-one

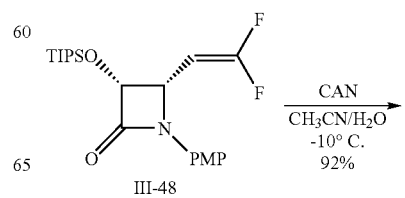

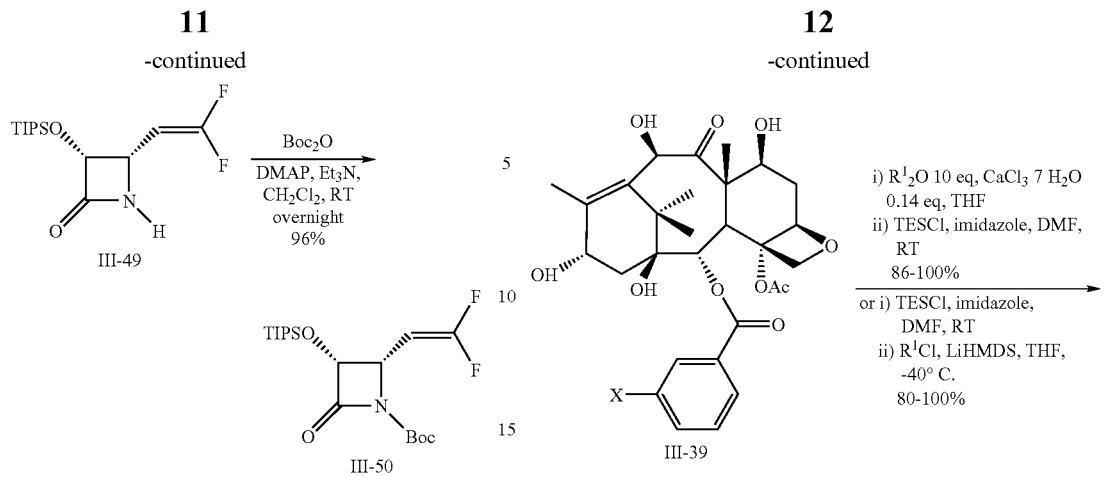

Example 2

Synthesis of C-3' Difluorovinyl Second-Generation Taxoids

The synthesis of baccatin core was performed using literature methods starting from 10-DAB, yielding III-41 or III-43 in high yields (Scheme III-25).

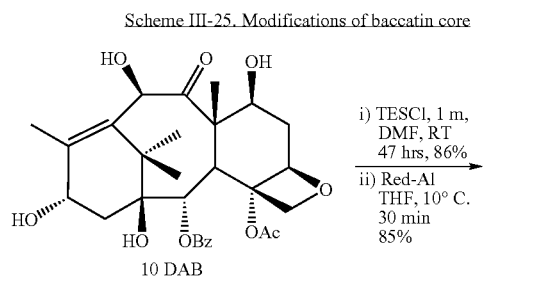

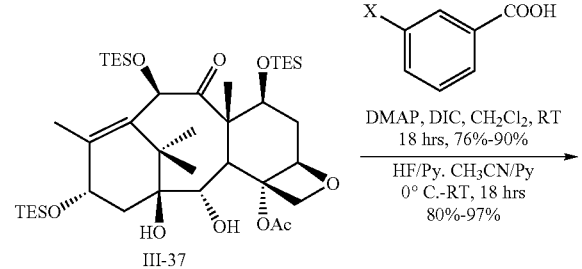

X = MeO, F, N$_3$, Cl

The ring-opening coupling of β-lactams with modified baccatins was carried out at −40° C. in THF using LiHMDS. The subsequent removal of the silyl protecting groups by HF/pyridine gave the corresponding new difluorovinyl-taxoids III-51 in fairly good overall yields (Scheme III-26).

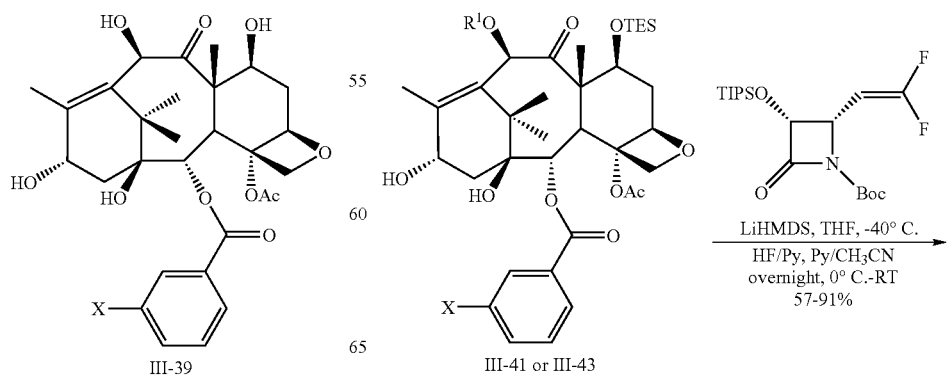

13

-continued

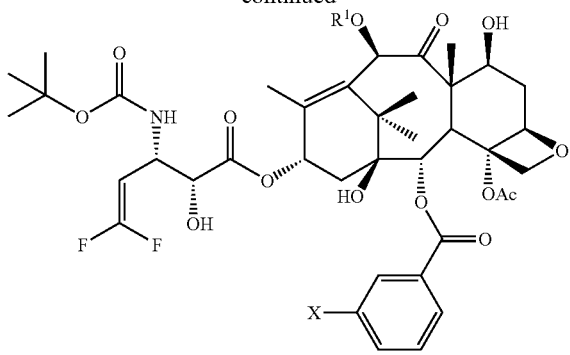

III-51a-y
R¹ = MeCO, EtCO, c-PrCO, (Me)₂NCO, MeOCO,
X = a) MeO, b) F, c) Cl, d) N₃,

Example 3

1-(4-Methoxyphenyl)-3-triisopropylsilanyloxy-4-(2,2-difluorovinyl)azetidin-2-one (III-48)

To a solution of dibromodifluoromethane (1.97 mL, 12.79 mmol) in THF (85 mL) were added hexamethylphosphorous triamide (4.79 mL, 25.56 mmol) and Zn (1.67 g, 25.56 mmol) at −78° C. The mixture was allowed to warm slowly to −10° C. The mixture was stirred for additional 30 min at −10° C. and ether was added to the reaction mixture. The ether layer was decanted and the residue was washed with dichloromethane and water. The combined organic layers were washed with saturated copper sulfate solution until the blue color stayed, and dried over MgSO₄. The filtrate was concentrated under reduced pressure to give yellow oil. Crude material was purified by flash chromatography on silica gel to yield III-48 (688 mg, 68%): $^1$H NMR (CDCl₃, 300 MHz): δ 1.08-1.15 (21H, m), 3.79 (3H, s), 4.54 (1H, ddd, J=1.5, 6.3, 16.5 Hz), 4.83 (1H, m), 5.14 (1H, d, J=5.1 Hz), 6.87 (2H, d, J=9.0 Hz), 7.32 (2H, d, J=9.0 Hz); $^{13}$C NMR (CDCl₃, 75.5 MHz): δ 12.1, 17.9, 54.1 (d, J=8.5 Hz), 55.8, 75.8 (dd, J=5.0, 22.1 Hz), 76.9, 77.4, 114.8, 118.6, 130.9, 156.7, 164.9; $^{19}$F NMR (282 MHz, CDCl₃): 8-80.80 (d, 1F, J=32.7 Hz), −86.34 (dd, 1F, J=2.8 Hz, J=28.2). LRMS (FAB+, m/z): Calcd. for C₂₁H₃₁F₂NO₃Si.H+, 412.2114; Found, 412.2127.

Example 4

3-Triisopropylsiloxy-4-(2,2-difluorovinyl)azetidin-2-one (III-49)

To a solution of N-PMP-β-lactam (688 mg, 1.67 mmol) in acetonitrile (50 mL) and water (10 mL), was added dropwise a solution of ceric ammonium nitrate (3.74 g, 6.69 mmol) in water (40 mL). The reaction mixture was stirred for 2 h. Work up with water and saturated Na₂SO₃ solution, The aqueous layer was extracted with EtOAc, and the combined organic layer was washed with water, dried over MgSO₄ and concentrated. The crude product was purified on a silica gel column to yield the β-lactam III-49 as a pale yellow oil (469 mg, 92% yield): $^1$H NMR (CDCl₃, 400 MHz): δ 1.03-1.18 (21H, m), 4.44-4.54 (2H, m), 5.04 (1H, dd, J=1.6, 2.4 Hz), 6.59 (1H, bs); $^{13}$C NMR (CDCl₃, 100 MHz): δ 12.1, 17.8 (d, J=4.6 Hz), 50.4 (d, J=7.6 Hz), 77.1 (dd, J=15.9, 23.5 Hz), 79.3, 157.6 (t, J=289.9 Hz), 169.4; $^{19}$F NMR (282 MHz, CDCl₃): β-82.33 (d, 1F, J=34.7 Hz), −87.50 (dd, 1F, J=9.3, 25.7 Hz).

14

Example 5

1-(tert-Butoxycarbonyl)-3-triisopropylsiloxy-4-(2,2-difluorovinyl)azetidin-2-one (III-50)

To a solution of 4-(2,2-difluorovinyl)-β-lactam III-49 (469 mg, 1.54 mmol), triethylamine (0.75 mL, 4.62 mmol), and DMAP (43 mg, 0.35 mmol) in CH₂Cl₂ (9 mL), was added Boc₂O (398 mg, 1.77 mmol) at room temperature. The reaction mixture was stirred for 18 hours and quenched with water. The reaction mixture was diluted with ethylacetate (EtOAc) and the organic layer was washed with brine, dried over MgSO₄, and concentrated under reduced pressure. Crude material was purified by flash chromatography on silica gel to give 1-Boc-4-(2,2-difluorovinyl)-β-lactam III-50 as yellow oil (599 mg, 96% yield): $[α]_D^{20}$ +24.17 (c 14.4, CHCl₃); $^1$H NMR (CDCl₃, 400 MHz): δ 1.04-1.17 (21H, m), 1.49 (9H, s), 4.49 (1H, ddd, J=1.6, 13.8, 23.7 Hz), 4.75 (1H, dddd, J=0.9, 2.4, 5.1, 9.0 Hz), 5.04 (1H, d, J=5.7 Hz), 6.59 (1 H, bs); $^{13}$C NMR (CDCl₃, 100 MHz): δ 12.0, 17.8 (d, J=5.3 Hz), 28.2, 53.6 (d, J=8.4 Hz), 74.5 (dd, J=10.6, 26.5 Hz), 77.2, 83.9, 147.9, 158.5 (t, J=292.2 Hz), 165.3; $^{19}$F NMR (282 MHz, CDCl₃): δ −81.20 (d, 1F, J=31.0 Hz), −85.83 (dd, 1F, J=5.6 Hz, J=29.3). HRMS (FAB+, m/z): Calcd. For C₁₉H₃₃F₂NO₄Si.Na+, 428.2039. Found, 428.2050.

Example 6

10-Acetyl-3'-dephenyl-3'-(2,2-difluorovinyl)docetaxel, SB-T-12851 (III-51a)

Yield 83%; white solid; mp 155-160° C.; $[α]_D^{20}$ −74.83 (c 2.86, CHCl₃); $^1$H NMR (CDCl₃, 400 MHz): δ 1.15 (3H, s, C-16), 1.25 (3H, m, C-17), 1.30 (9H, s, Boc), 1.68 (3H, s, H-19), 1.75 (bs, 1H, OH), 1.88 (4H, m, H-6b, H-18), 2.24 (3H, s, 10-OAc), 2.33 (2H, m, H-14), 2.39 (3H, s, 4-OAc), 2.49 (1H, d, J=3.6 Hz, OH), 2.55 (1H, ddd, 0.1=6.4, 9.6, 14.8 Hz, H-6a), 3.52 (1H, d, J=5.6 Hz, OH), 3.81 (1H, d, J=7.2 Hz, H-3), 4.17 (1H, d, J=8.4 Hz, H-20b), 4.28 (1H, s, J=2.8 Hz, H-2'), 4.31 (1H, d, J=8.4 Hz, H-20a), 4.44 (1H, m, H-7), 4.58 (1H, ddd, J=1.2, 9.6, 24.8 Hz, H-3'-vinyl), 4.87 (1H, t, J=8.8 Hz, H-3'), 4.96 (2H, d, J=9.6 Hz, H-5, NH-3'), 5.66 (1H, d, J=7.2 Hz, H-2), 6.24 (1H, t, J=8.8 Hz, H-13), 6.30 (1H, s, H-10), 7.49 (2H, t, J=7.6 Hz), 7.61 (1H, t, J=7.2 Hz), 8.11 (2H, d, J=7.6 Hz); $^{13}$C NMR (CDCl₃, 100 MHz) δ 9.8, 14.4, 15.1, 21.1, 22.1, 22.5, 26.9, 28.3, 35.7 (d, J=13.7 Hz), 43.5, 45.7, 48.2, 58.8, 72.4, 72.9, 75.8, 76.7, 79.3, 80.7, 81.3, 84.6, 128.9, 129.3, 130.4, 133.4, 133.9, 142.4, 155.1, 156.7, 158.0, 167.3, 170.5, 171.5, 172.7, 203.9; 19F NMR, (CDCl₃, 282 MHz) δ −84.29 (1F, dd, J=25.7, 36.4 Hz), −86.22 (1F, dd, J=34.7 Hz); HRMS (FAB+, m/z): Calcd. for C₄₁H₅₁F₂NO₁₅.H+, 836.3300; Found, 836.3278.

Example 7

3'-dephenyl-3'-(2,2-difluorovinyl)-10-cyclopropanecarbonyl-docetaxel, SB-T-12852 (III-51b)

Yield 88%; white solid; mp 171-177° C.; $[α]_D^{20}$ −73.71 (c 5.44, CHCl₃); $^1$H NMR (CDCl₃, 400 MHz): δ 0.98 (2H, m, CH₂-c-Pr), 1.13 (2H, m, CH₂-c-Pr), 1.15 (3H, s, C-16), 1.26 (3H, m, C-17), 1.30 (9H, s, Boc), 1.66 (3H, s, H-19), 1.78 (2H, m, OH, CH-c-Pr), 1.87 (411, m, H-6b, H-18), 2.31 (2H, m, H-14), 2.38 (311, s, 4-OAc), 2.53 (1H, ddd, J=6.8, 10.0, 15.2 Hz, H-6a), 2.59 (1H, d, J=3.2 Hz, OH), 3.57 (1H, bs, OH), 3.80 (1H, d, J=6.8 Hz, H-3), 4.17 (1H, d, J=8.4 Hz, H-20b), 4.28 (2H, m, H-2', H-20a), 4.40 (1H, m, H-7), 4.58 (1H, ddd, J=1.6, 9.6, 24.8 Hz, H-3'-vinyl), 4.87 (1H, t, J=8.8 Hz, H-3'), 4.97 (2H, m, H-5, NH'), 5.66 (1H, d, J=7.2 Hz, H-2), 6.24 (1H, t, J=8.0 Hz, H-13), 6.29 (1H, s, H-10), 7.49 (2H, t, J=7.6 Hz), 7.60 (1H, t, j=7.6 Hz), 8.11 (2H, d, J=7.2 Hz); $^{13}$C NMR (CDCl$_3$, 100 MHz) δ 9.4, 9.6, 9.8, 13.2, 22.5, 27.0, 28.3, 35.7, (d, J=5.3 Hz), 43.5, 45.9, 48.2, 58.8, 72.4, 72.9, 73.3, 75.3, 75.6, 76.6, 79.3, 80.7, 81.3, 84.7, 128.9, 129.3, 130.4, 133.4, 133.9, 142.4, 155.1, 156.7, 167.3, 170.5, 172.6, 175.3, 204.0; $^{19}$F NMR, (CDCl$_3$, 282 MHz) δ-84.32 (1F, dd, J=25.4, 36.4 Hz), −86.30 (1F, dd, J=36.7 Hz); HRMS (FAB+, m/z): Calcd. for C$_{43}$H$_{53}$F$_2$NO$_{15}$.H+, 862.3456; Found, 862.3445.

Example 8

3'-Dephenyl-3'-(2,2-difluorovinyl)-10-propanoyldocetaxel, SB-T-12853 (III-51c):

Yield 64%; white solid; mp 175-181° C.; [α]$_D^{20}$ −82.83 (c 5.01, CHCl$_3$); $^1$H NMR (CDCl$_3$, 400 MHz): δ 1.14 (3H, s, H-16), 1.24 (6H, m, H-17, H-10-CH$_3$), 1.30 (9H, s, Boc), 1.67 (3H, s, H-19), 1.78 (1H, m, OH), 1.87 (4H, m, H-6b, H-18), 2.31 (2H, m, H-14), 2.38 (3H, s, 4-OAc), 2.53 (4H, m, H-6a, H-10, CH$_2$, OH), 3.55 (1H, bs, OH), 3.81 (1H, d, J=6.8 Hz, H-3), 4.17 (1H, d, J=8.4 Hz, H-20b), 4.29 (2H, m, H-2', H-20a), 4.39 (1H, m, H-7), 4.56 (1H, ddd, J=1.6, 9.6, 24.8 Hz, H-3'-vinyl), 4.86 (1H, t, J=8.8 Hz, H-3'), 4.96 (2H, m, H-5, NH'), 5.66 (1H, d, J=7.2 Hz, H-2), 6.25 (1H, t, J=8.4 Hz, H-13), 6.30 (1H, s, H-10), 7.49 (2H, t, J=7.6 Hz), 7.60 (1H, t, J=7.2 Hz), 8.11 (2H, d, J=7.2 Hz); $^{13}$C NMR (CDCl$_3$, 100 MHz) δ 9.2, 9.8, 15.1, 22.1, 22.5, 26.9, 27.8, 28.4, 35.7 (d, J=12.9 Hz), 43.5, 45.9, 48.2, 58.8, 72.2, 72.4, 72.9, 73.3, 75.3, 75.6, 76.6, 77.4, 79.3, 80.7, 81.3, 84.6, 128.9, 129.3, 130.4, 133.5, 133.9, 142.2, 155.1, 156.7, 167.3, 170.5, 172.6, 174.8, 203.9; $^{19}$F NMR, (CDCl$_3$, 282 MHz) δ −84.31 (1F, dd, J=23.7, 34.7 Hz), −86.23 (1F, dd, J=36.4 Hz); HRMS (FAB+, m/z): Calcd. For C$_{42}$H$_{53}$F$_2$NO$_{15}$.H+, 850.3456; Found 850.3450.

Example 9

3'-Dephenyl-3'-(2,2-difluorovinyl)-10-dimethylcarbamoyldocetaxel, SB-T-12854 (III-51d)

Yield 84%; white solid; mp 166-170° C.; [α]$_D^{20}$ −70.48 (c 6.3, CHCl$_3$); $^1$H NMR (CDCl$_3$, 400 MHz): δ 1.15 (3H, s, H-16), 1.25 (3H, m, H-17), 1.30 (9H, s, Boc), 1.67 (3H, s, H-19), 1.84 (1H, m, OH), 1.89 (4H, m, H-6b, H-18), 2.31 (2H, m, H-14), 2.38 (3H, s, 4-OAc), 2.53 (1H, ddd, J=6.8, 9.6, 15.2 Hz, H-6a), 3.64 (1H, d, J=5.6 Hz, OH), 3.80 (1H, d, J=6.8 Hz, H-3), 4.17 (1H, d, J=8.4 Hz, H-20b), 4.29 (2H, m, H-2', H-20a), 4.44 (1H, m, H-7), 4.57 (1H, dd, J=10.0, 25.2 Hz, H-3'-vinyl), 4.86 (1H, t, J=8.8 Hz, H-3'), 4.97 (1H, d, J=9.2 Hz, NH-3'), 5.02 (1H, d, J=9.6 Hz, H-5), 5.66 (1H, d, J=7.2 Hz, H-2), 6.24 (2H, m, Hz, H-13, H-10), 7.49 (2H, t, J=7.6 Hz), 7.59 (1H, t, J=7.2 Hz), 8.10 (2H, d, J=7.6 Hz); $^{13}$C NMR (CDCl$_3$, 100 MHz) δ 9.6, 15.1, 22.1, 22.5, 27.1, 28.3, 35.6 (d, J=12.1 Hz), 36.3, 36.8, 43.5, 45.8, 48.2, 58.7, 72.6, 72.9, 73.3, 75.4, 76.3, 76.7, 77.4, 79.4, 80.6, 81.3, 84.6, 128.9, 129.4, 130.4, 133.7, 133.9, 142.7, 155.1, 156.3, 156.5, 167.3, 170.4, 171.3, 203.9; $^{19}$F NMR, (CDCl$_3$, 282 MHz) δ −84.31 (1F, dd, J=25.7, 37.2 Hz), −86.23 (1F, dd, J=36.4 Hz); HRMS (FAB+, m/z): Calcd. For C$_{42}$H$_{54}$F$_2$N$_2$O$_{15}$.H+, 865.3565; Found 865.3562.

Example 10

3'-Dephenyl-3'-(2,2-difluorovinyl)-10-methoxycarbonyldocetaxel, SB-T-12855 (III-51e)

Yield 90%; white solid; mp 144-148° C.; [α]$_D^{20}$ −77.06 (c 6.8, CHCl$_3$); $_1$H NMR (CDCl$_3$, 400 MHz): δ 1.15 (3H, s, H-16), 1.24 (3H, m, H-17), 1.29 (9H, s, Boc), 1.68 (3H, s, H-19), 1.78 (1H, m, OH), 1.88 (1H, m, H-6b), 1.91 (3H, s, H-18), 2.31 (2H, m, H-14), 2.39 (3H, s, 4-OAc), 2.53 (2H, m, H-6a, OH), 3.55 (1H, d, J=5.6 Hz, OH), 3.78 (1H, d, J=7.2 Hz, H-3), 3.86 (3H, s, H-10-MeO), 4.17 (1H, d, J=8.4 Hz, H-20b), 4.29 (2H, m, H-2', H-20a), 4.38 (1H, m, H-7), 4.57 (1H, ddd, J=1.6, 9.6, 24.8 Hz, H-3'-vinyl), 4.86 (1H, t, J=8.8 Hz, H-3'), 4.96 (2H, m, H-5, NH'), 5.66 (1H, d, J=6.8 Hz, H-2), 6.11 (1H, s, H-10), 6.23 (2H, t, J=8.0 Hz, H-13), 7.49 (2H, t, J=7.6 Hz), 7.60 (1H, t, J=7.2 Hz), 8.10 (2H, d, J=7.2 Hz); $^{13}$C NMR (CDCl$_3$, 100 MHz) δ 9.7, 15.2, 22.1, 22.5, 26.8, 28.3, 35.8 (d, J=23.5 Hz), 43.4, 45.9, 48.2, 55.8, 58.8, 72.1, 72.3, 72.8, 73.3, 75.2, 76.7, 77.4, 78.4, 79.2, 80.7, 81.2, 84.6, 128.9, 129.3, 130.4, 133.0, 133.9, 143.2, 155.1, 155.9, 156.5, 167.3, 170.6, 172.3, 204.1; $^{19}$F NMR, (CDCl$_3$, 282 MHz) δ −84.30 (1F, dd, J=23.7, 34.7 Hz), −86.22 (1F, dd, 34.7 Hz); HRMS (FAB+, m/z): Calcd. for C$_{41}$H$_{51}$F$_2$NO$_{16}$.H+, 852.3249; Found 852.3227.

Example 11

3'-Dephenyl-3'-(2,2-difluorovinyl)-2-debenzoyl-2-(3-fluorobenzoyl)-10-acetyldocetaxel, SB-T-12851-2 (III-51f)

Yield 72%; white solid; [α]$_D^{20}$ −73.29 (c, 7.0 CHCl$_3$); $^1$H NMR (CDCl$_3$, 400 MHz): δ 1.15 (3H, s, C-16), 1.26 (1H, m, C-17), 1.31 (9H, s, Boc), 1.68 (4H, s, H-19, OH), 1.89 (4H, m, H-6b, H-18), 2.24 (3H, s, 10-OAc), 2.33 (2H, m, H-14), 2.39 (3H, s, 4-OAc), 2.47 (1H, bs, OH), 2.56 (1H, ddd, J=7.0, 9.5, 15.0 Hz, H-6a), 3.46 (1H, bs, OH), 3.82 (1H, d, J=7.0 Hz, H-3), 4.16 (1H, d, J=8.5 Hz, H-20b), 4.28 (1H, s, H-2'), 4.31 (1H, d, J=8.5 Hz, H-20a), 4.42 (1H, dd, J=6.5, 11.0 Hz, H-7), 4.58 (1H, ddd, J=1.0, 9.0, 26.0 Hz, H-3' vinyl), 4.90 (2H, m, H-3', NH-3'), 4.97 (1H, dd, J=2.0, 9.0, H-5), 5.64 (1H, d, J=7.0 Hz, H-2), 6.23 (1H, t, J=8.0 Hz, H-13), 6.30 (1H, s, H-10), 7.31 (1H, dt, J=2.0, 8.0 Hz), 7.49 (1H, ddd, J=6.0, 8.5, 13.5 Hz), 7.80 (1H, d, J=9.0 Hz), 7.91 (1H, d, J=7.5 Hz); $^{13}$C NMR (CDCl$_3$, 100 MHz) δ 9.5, 14.8, 20.8, 21.8, 22.2, 26.7, 28.1, 35.5 (d, J=11.8 Hz), 43.2, 45.6, 58.5, 72.1, 72.5, 73.1, 75.5, 76.3, 79.1, 80.4, 80.9, 84.4, 117.0 (J=23.2 Hz), 120.8 (J=21.1 Hz), 125.9, 130.4 (J=7.8 Hz), 131.2 (J=7.4 Hz), 132.9, 142.2, 154.9, 156.7, 160.9, 164.2, 165.9, 170.2, 171.2, 203.5; $^{19}$F NMR, (CDCl$_3$, 282 MHz) δ −84.23 (1F, dd, J=25.7, 34.7 Hz), −86.21 (1F, dd, J=36.7 Hz), −111.7 (1F, dd, J=9.3, 14.6 Hz); HRMS (FAB+, m/z): Calcd. for C$_{41}$H$_{50}$F$_3$NO$_{15}$.H+, 854.3205; Found, 854.3207.

Example 12

3'-Dephenyl-3'-(2,2-difluorovinyl)-2-debenzoyl-2-(3-fluorobenzoyl)-10-cyclopropanecarbonyldocetaxel, SB-T-12852-2 (III-51g)

Yield 78%; white solid; [α]$_D^{20}$-77.04 (c 7.1, CHCl$_3$); $^1$H NMR (CDCl$_3$, 500 MHz): δ 0.99 (2H, m, CH$_2$-c-Pr), 1.12 (2H, m, CH$_2$-c-Pr), 1.15 (3H, s, C-16), 1.26 (3H, m, C-17), 1.30 (9H, s, Boc), 1.66 (3H, s, H-19), 1.77 (2H, m, OH, CH-c-Pr), 1.86 (1H, m, H-6b), 1.87 (3H, s, H-18), 2.33 (2H, m, H-14), 2.39 (3H, s, 4-OAc), 2.53 (1H, ddd, J=7.0, 9.5, 15.5 Hz, H-6a), 2.61 (1H, bs, OH), 3.55 bs, OH), 3.80 (1H, d, J=7.0 Hz, H-3), 4.17 (1H, d, J=8.0 Hz, H-20b), 4.28 (1H, s, H-2'), 4.29 (1H, d, J=8.0 Hz, H-20a), 4.40 (1H, dd, J=7.0, 10.5 Hz, H-7), 4.58 (1H, dd, J=8.5, 23.5 Hz, H-3' vinyl), 4.86 (1H, m, H-3'), 4.97 (2H, m, H-5, NH'), 5.63 (1H, d, J=7.0 Hz, H-2), 6.24 (1H, t, J=9.5 Hz, H-13), 6.29 (1H, s, H-10), 7.49 (2H, dt, J=2.5, 8.5 Hz), 7.60 (1H, ddd, J=6.0, 8.0, 13.5 Hz), 7.78 (1H, d, J=9.5 Hz), 7.90 (1H, d, J=7.5 Hz); $^{13}$C NMR (CDCl$_3$, 125 MHz) δ 9.2, 9.5, 13.0, 14.7, 21.9, 22.2, 26.7, 28.1, 35.5, (d, 5.4 Hz), 43.2, 45.6, 48.0, 58.5, 72.1, 72.5, 73.1, 75.3, 75.5, 76.3, 79.1, 80.4, 80.9, 84.4, 117.0 (d, J=23.8 Hz), 120.8 (d, J=21.2 Hz), 125.9, 130.4 (d, J=7.7 Hz), 131.3 (d, J=7.7 Hz), 133.0, 142.2, 154.8, 160.9, 164.2, 165.8, 170.2, 175.1, 203.7; $^{19}$F NMR, (CDCl$_3$, 282 MHz) δ −84.22 (1F, dd, J=23.7, 36.7 Hz), −86.20 (1F, d, J=34.7 Hz), −111.72 (1F, dd, J=9.3, 14.6 Hz); HRMS (FAB+, m/z): Calcd. for C$_{43}$H$_{52}$F$_3$NO$_{15}$.H+, 880.3362; Found, 880.3346.

Example 13

3'-Dephenyl-3'-(2,2-difluorovinyl)-2-debenzoyl-2-(3-fluorobenzoyl)-10-propanoyldocetaxel, SB-T-12853-2 (III-51h)

Yield 71%; white solid; $[\alpha]_D^{20}$ −71.57 (c 8.3, CHCl$_3$); $^1$H NMR (CDCl$_3$, 500 MHz): δ 1.14 (3H, s, H-16), 1.24 (6H, m, H-17, H-10-CH$_3$), 1.31 (9H, s, Boc), 1.67 (3H, s, H-19), 1.72 (1H, bs, OH), 1.88 (4H, m, H-6b, H-18), 2.32 (2H, m, H-14), 2.39 (3H, s, 4-OAc), 2.53 (3H, m, H-6a, H-10, CH$_2$), 3.51 (1H, bs, OH), 3.82 (1H, d, J=7.0 Hz, H-3), 4.16 (1H, d, J=8.5 Hz, H-20b), 4.28 (1H, d, J=1.5 Hz, H-2'), 4.30 (1H, d, J=8.5 Hz, H-20a), 4.42 (1H, dd, J=6.5, 10.5 Hz, H-7), 4.58 (1H, ddd, J=1.5, 9.0, 24.5 Hz, H-3'), 4.87 (1H, m, H-3'), 4.96 (2H, m, H-5, NH'-3'), 5.64 (1H, d, J=6.5 Hz, H-2), 6.23 (1H, t, J=8.0 Hz, H-13), 6.31 (1H, s, H-10), 7.31 (111, dt, J=2.0, 7.0 Hz), 7.48 (1H, ddd, J=5.5, 7.5, 13.0 Hz), 7.80 (1H, d, J=8.5 Hz), 7.91 (1H, d, J=7.5 Hz); $^{13}$C NMR (CDCl$_3$, 125 MHz) δ 8.9, 9.5, 14.8, 21.9, 22.2, 26.7, 27.5, 28.1, 35.5 (d, J=10.3 Hz), 43.2, 45.6, 58.5, 72.1, 72.5, 73.1, 75.3, 75.4, 76.3, 79.1, 80.9, 84.4, 116.9 (d, J=23.8 Hz), 120.8 (d, J=21.2 Hz), 125.9, 130.4 (d, J=7.5 Hz), 131.3 (d, J=7.4 Hz), 133.0, 142.1, 154.6, 160.9, 164.2, 165.8, 170.2, 174.6, 203.6; $^{19}$F NMR, (CDCl$_3$, 282 MHz) δ −84.24 (1F, dd, J=23.9, 34.9 Hz), −86.22 (1F, d, J=36.4 Hz); HRMS (FAB+, m/z): Calcd. for C$_{42}$H$_{52}$F$_3$NO$_{15}$.H+, 868.3362; Found 868.3352.

Example 14

3'-Dephenyl-3'-(2,2-difluorovinyl)-2-debenzoyl-2-(3-fluorobenzoyl)-10-dimethylcarbamoyldocetaxel, SB-T-12854-2 (III-51i)

Yield 71%; white solid; $[\alpha]_D''$-85.33 (c 1.5, CHCl$_3$); $^1$H NMR (CDCl$_3$, 500 MHz): δ 1.16 (3H, s, H-16), 1.26 (3H, m, H-17), 1.31 (9H, s, Boc), 1.60 (1H, OH), 1.67 (3H, s, H-19), 1.84 (1H, m, OH), 1.89 (1H, m, H-6b), 1.91 (3H, s, H-18), 2.33 (2H, m, H-14), 2.40 (3H, s, 4-OAc), 2.55 (1H, ddd, J=6.0, 9.5, 14.5 Hz, H-6a), 2.97 (3H, s, NMe), 3.05 (3H, s, N-Me), 3.40 (1H, s, OH), 3.82 (1H, d, J=7.0 Hz, H-3), 4.17 (1H, d, J=7.5 Hz, H-20b), 4.29 (1H, s, H-2'), 4.31 (1H, d, J=7.5 Hz, H-20a), 4.45 (1H, dd, J=6.0, 10.5 Hz, H-7), 4.58 (1H, m, H-3' vinyl), 4.87 (2H, bs, H-3', NH-3'), 4.99 (1H, d, J=8.0 Hz, H-5), 5.64 (1H, d, J=7.0 Hz, H-2), 6.26 (2H, m, Hz, H-13, H-10), 7.32 (2H, dt, J=2.0, 8.0 Hz), 7.49 (1H, ddd, J=6.0, 8.5, 13.5 Hz), 7.81 (1H, d, J=9.5 Hz), 7.92 (1H, d, J=8.0 Hz); $^{13}$C NMR (CDCl$_3$, 125 MHz) δ 9.3, 14.7, 22.3, 26.9, 28.1, 35.4 (d, J=6.0 Hz), 36.0, 36.6, 43.2, 45.5, 58.5, 72.4, 72.7, 73.1, 75.6, 76.1, 76.4, 77.2, 79.3, 80.4, 81.1, 84.6, 110.7 (d, J=15.1 Hz), 120.8 (d, J=21.2 Hz), 125.9, 130.4 (d, J=7.7 Hz), 131.3 (d, J=7.5 Hz), 133.9, 142.1, 155.1, 157.4, 161.2, 164.1, 166.1, 170.2, 172.3, 205.5; $^{19}$F NMR, (CDCl$_3$, 282 MHz) δ-84.13 (1F, dd, J=25.4, 36.4 Hz), −86.13 (1F, d, J=36.6 Hz), −111.73 (1F, dd, J=9.3, 14.6 Hz); HRMS (FAB+, m/z): Calcd. for C$_{42}$H$_{53}$F$_3$N$_2$O$_{15}$.H+, 883.3471; Found 883.3433.

Example 15

3'-Dephenyl-3'-(2,2-difluorovinyl)-2-debenzoyl-2-(3-fluorobenzoyl)-10-methoxycarbonyldocetaxel, SB-T-12855-2 (III-51j)

Yield 72%; white solid; $[\alpha]_D^{20}$ −70.31 (c 6.5, CHCl$_3$); $^1$H NMR (CDCl$_3$, 500 MHz): δ 1.15 (3H, s, H-16), 1.25 (3H, m, H-17), 1.29 (9H, s, Boc), 1.65 (1H, bs, OH), 1.69 (3H, s, H-19), 1.88 (1H, m, H-6b), 1.92 (3H, s, H-18), 2.31 (2H, m, H-14), 2.39 (3H, s, 4-OAc), 2.46 (1H, bs, OH), 2.57 (1H, ddd, J=6.0, 9.0, 15 Hz, H-6a), 3.48 (1H, bs, OH), 3.79 (1H, d, J=7.5 Hz, H-3), 3.87 (3H, s, H-10-MeO), 4.16 (1H, d, J=8.5 Hz, H-20b), 4.28 (1H, s, H-2'), 4.31 (1H, d, J=8.5 Hz, H-20a), 4.39 (1H, dd, J=7.0, 10.5 Hz, H-7), 4.58 (1H, dd, J=9.0, 24.5 Hz, H-3' vinyl), 4.87-4.94 (2H, m, H-3', NH-3'), 4.97 (1H, d, J=8.0 Hz, H-5), 5.65 (1H, d, J=7.0 Hz, H-2), 6.12 (1H, s, H-10), 6.23 (2H, t, J=9.0 Hz, H-13), 7.31 (1H, dt, J=2.5, 8.5 Hz), 7.49 (1H, ddd, J=5.0, 7.5, 13.5 Hz,), 7.79 (1H, d, J=8.5 Hz), 7.91 (1H, d, J=8.0 Hz); $^{13}$C NMR (CDCl$_3$, 125 MHz) δ9.4, 14.9, 21.8, 22.2, 26.6, 28.1, 35.3, 35.6, 43.1, 45.6, 47.9, 55.6, 58.5, 72.1, 72.5, 73.1, 75.4, 76.3, 78.2, 79.2, 80.5, 81.0, 84.6, 117.1 (d, J=23.5 Hz), 120.8 (d, J=21.4 Hz), 126.0, 130.4 (d, J=8.0 Hz), 131.3 (d, J=7.5 Hz), 132.7, 143.1, 154.9, 155.7, 160.9, 164.2, 165.9, 170.3, 203.8; $^{19}$F NMR, (CDCl$_3$, 282 MHz) δ −84.15 (1F, dd, J=25.4, 36.4 Hz), −86.17 (1F, d, J=36.7 Hz), −111.71 (1F, dd, J=9.3, 14.6 Hz); HRMS (FAB$^+$, m/z): Calcd. for C$_{41}$H$_{50}$F$_3$NO$_{16}$.H$^+$, 870.3154; Found 870.3146.

Example 16

3'-Dephenyl-3'-(2,2-difluorovinyl)-2-debenzoyl-2-(3-chlorobenzoyl)-10-acetyldocetaxel, SB-T-12851-4 (III-51k)

Yield 57%; white solid; mp ° C.; $[\alpha]_D^{20}$ −72.93 (c 4.1, CHCl$_3$); $^1$H NMR (CDCl$_3$, 500 MHz): δ 1.14 (3H, s, C-16), 1.25 (3H, m, C-17), 1.31 (9H, s, Boc), 1.67 (3H, s, H-19), 1.73 (1H, s, OH), 1.89 (4H, m, H-6b, H-18), 2.24 (3H, s, 10-OAc), 2.33 (2H, d, J=8.5 Hz, H-14), 2.39 (3H, s, 4-OAc), 2.51 (1H, d, J=3.5 Hz, OH), 2.55 (1H, ddd, J=6.5, 9.0, 15.0 Hz, H-6a), 3.51 (1H, bs, OH), 3.81 (1H, d, J=7.5 Hz, H-3), 4.15 (1H, d, J=8.5 Hz, H-20b), 4.29 (2H, m, H-2', H-20a), 4.41 (1H, dd, J=6.5, 11.0 Hz, H-7), 4.58 (1H, ddd, J=1.0, 10.0, 24.5 Hz, H-3' vinyl), 4.86 (1H, m, H-3'), 4.93 (1H, d, J=9.0 Hz, NH-3'), 4.98 (1H, d, J=7.5 Hz, H-5), 5.62 (1H, d, J=7.5 Hz, H-2), 6.21 (1H, t, J=9.5 Hz, H-13), 6.30 (1H, s, H-10), 7.45 (1H, t, J=7.5 Hz), 7.58 (1H, dd, J=1.5, 8.5 Hz), 8.00 (1H, d, J=7.5 Hz), 8.12 (1H, s); $^{13}$C NMR (CDCl$_3$, 125 MHz) δ 9.5, 14.8, 20.8, 21.8, 22.1, 26.7, 28.1, 35.4 (d, J=16.7 Hz), 43.1, 45.6, 58.5, 72.1, 72.5, 73.1, 75.5, 76.3, 79.2, 80.4, 80.9, 84.3, 128.2, 130.0, 130.3, 130.9, 132.9, 134.8, 142.2, 154.8, 165.7, 170.2, 171.2, 203.5; $^{19}$F NMR, (CDCl$_3$, 282 MHz) δ-84.15 (1F, dd, J=25.7, 36.7 Hz), −86.12 (1F, dd, J=36.7 Hz); HRMS (FAB+, m/z): Calcd. for C$_{41}$H$_{50}$ClF$_2$NO$_{15}$.H$^+$, 870.2910; Found, 870.2891.

Example 17

3'-Dephenyl-3'-(2,2-difluorovinyl)-2-debenzoyl-2-(3-chlorobenzoyl)-10-cyclopropanecarbonyldocetaxel, SB-T-12852-4 (III-51l)

Yield 73%; white solid; mp ° C.; $[\alpha]_D^{20}$ −78.97 (c 5.8, CHCl$_3$); $^1$H NMR (CDCl$_3$, 400 MHz): δ 1.02 (2H, m, CH$_2$- c-Pr), 1.15 (2H, m, CH$_2$-c-Pr), 1.16 (3H, s, C-16), 1.28 (3H, m, C-17), 1.32 (9H, s, Boc), 1.68 (3H, s, H-19), 1.70 (1H, bs, OH), 1.80 (1H, m, CH-c-Pr), 1.86-1.89 (1H, m, H-6b), 1.89 (3H, s, H-18), 2.33 (2H, m, H-14), 2.41 (3H, s, 4-OAc), 2.56 (1H, ddd, J=7.0, 9.0, 15.0 Hz, H-6a), 2.59 (1H, bs, OH), 3.51 (1H, bs, OH), 3.82 (1H, d, J=7.0 Hz, H-3), 4.16 (1H, d, J=8.5 Hz, H-20b), 4.29 (1H, s, H-2'), 4.31 (1H, d, J=8.5 Hz, H-20a), 4.41 (1H, dd, J=7.0, 10.5 Hz, H-7), 4.59 (1H, dd, J=9.0, 25.0 Hz, H-3' vinyl), 4.89 (1H, m, H-3'), 4.98 (2H, m, H-5, NH'), 5.63 (1H, d, J=7.0 Hz, H-7), 6.24 (1H, t, J=9.0 Hz, H-13), 6.31 (1H, s, H-10), 7.46 (2H, t, J=8.5 Hz), 7.60 (1H, dd, J=1.0, 7.0 Hz), 8.01 (1H, d, J=7.5 Hz), 8.13 (1H, s); $^{13}$C NMR (CDCl$_3$, 100 MHz) δ 9.2, 9.4, 13.0, 14.9, 21.9, 22.2, 26.7, 28.1, 35.4, (d, J=7.9 Hz), 43.2, 45.6, 48.0, 58.5, 72.1, 72.6, 73.1, 75.3, 75.5, 76.3, 77.2, 79.2, 80.4, 81.0, 84.4, 128.3, 130.0, 130.3, 130.9, 133.0, 133.7, 134.8, 142.3, 154.8, 165.7, 170.2, 175.1, 203.7; $^{19}$F NMR (CDCl$_3$, 282 MHz) 5-84.15 (1F, dd, J=25.7, 34.7 Hz), −86.16 (1F, d, J=36.7 Hz); HRMS (FAB$^+$, m/z): Calcd. for C$_{43}$H$_{52}$ClF$_2$NO$_{15}$.H$^+$, 896.3066.
Found, 896.3036.

Example 18

3'-Dephenyl-3'-(2,2-difluorovinyl)-2-debenzoyl-2-(3-chlorobenzoyl)-10-propanoyldocetaxel, SB-T-12853-4 (III-51 m)

Yield 72%; white solid; [α]$_D^{20}$ −76.73 (c 4.9, CHCl$_3$); $^1$H NMR (CDCl$_3$, 500 MHz): δ 1.14 (3H, s, H-16), 1.22-1.25 (6H, m, H-17, H-10-CH$_3$), 1.31 (9H, s, Boc), 1.67 (3H, s, H-19), 1.71 (1H, s, OH), 1.86-1.91 (4H, m, H-6b, H-18), 2.32 (2H, m, H-14), 2.39 (3H, s, 4-OAc), 2.40-2.59 (3H, m, H-6a, H-10, CH$_2$), 3.49 (1H, bs, OH), 3.82 (1H, d, J=7.0 Hz, H-3), 4.15 (2H, d, J=8.5 Hz, H-20b), 4.29 (2H, H-2', H-20a), 4.40 (1H, dd, J=6.0, 10.5 Hz, H-7), 4.58 (1H, ddd, J=1.5, 9.0, 24.5 Hz, H-3'), 4.87 (1H, m, H-3'), 4.92 (1H, d, J=9.0 Hz, NH'-3'), 4.98 (1H, dd, J=1.5, 9.5 Hz, H-5), 5.62 (1H, d, J=7.5 Hz, H-2), 6.22 (1H, t, J=9.5 Hz, H-13), 6.31 (1H, s, H-10), 7.45 (1H, t, J=8.0 Hz), 7.45 (1H, ddd, J=1.0, 2.0, 8.0 Hz), 8.00 (1H, d, J=7.5 Hz), 8.12 (1H, s); $^{13}$C NMR (CDCl$_3$, 125 MHz) δ 8.9, 9.5, 14.9, 21.8, 22.2, 26.7, 27.5, 28.1, 35.5 (d, J 15.9 Hz), 43.2, 45.7, 58.5, 72.2, 72.6, 73.1, 75.3, 75.5, 76.3, 79.2, 80.4, 81.0, 84.4, 128.3, 130.1, 130.3, 130.9, 133.1, 133.7, 134.8, 142.1, 154.8, 165.7, 170.2, 174.6, 203.6; $^{19}$F NMR (CDCl$_3$, 282 MHz) 6-84.14 (1F, dd, J=23.7, 34.7 Hz), −86.13 (1F, d, J=36.7 Hz); HRMS (FAB$^+$, m/z): Calcd. for C$_{42}$H$_{52}$ClF$_2$NO$_{15}$.H$^+$, 884.3066; Found 884.3057.

Example 19

3'-Dephenyl-3'-(2,2-difluorovinyl)-2-debenzoyl-2-(3-chlorobenzoyl)-10-dimethylcarbamoyldocetaxel, SB-T-12854-4 (III-51n)

Yield 91%; white solid; mp ° C.; [α]$_D^{20}$ −88.09 (c 2.1, CHCl$_3$); $^1$H NMR (CDCl$_3$, 500 MHz): δ 1.17 (3H, s, H-16), 1.27 (3H, m, H-17), 1.33 (9H, s, Boc), 1.62 (1H, bs, OH), 1.69 (3H, s, H-19), 1.84 (1H, m, OH), 1.90 (1H, ddd, J=2.5, 11.5, 17.5 Hz, H-6b), 1.93 (3H, s, H-18), 2.34 (2H, m, H-14), 2.42 (3H, s, 4-OAc), 2.56 (1H, ddd, J=6.0, 9.0, 15.0 Hz, H-6a), 2.98 (3H, s, N-Me), 3.06 (3H, s, N-Me), 3.25 (1H, d, J=2.5 Hz, OH), 3.52 (1H, d, J=5.5 Hz, OH), 3.83 (1H, d, J=7.0 Hz, H-3), 4.18 (1H, d, J=8.5 Hz, H-20b), 4.29 (1H, s, H-2'), 4.32 (1H, d, J=8.5 Hz, H-20a), 4.46 (1H, dd, J=6.5, 11.0 Hz, H-7), 4.58 (1H, ddd, J=1.5, 10.0, 24.5 Hz, H-3' vinyl), 4.93 (2H, m, H-3', NH-3'), 5.01 (1H, d, J=10.0 Hz, H-5), 5.63 (1H, d, J=7.5 Hz, H-2), 6.25 (1H, t, J=9.0 Hz, H-13), 6.27 (1H, s, H-10), 7.47 (2H, t, J=7.5 Hz), 7.49 (1H, dd, J=1.0, 9.5 Hz), 7.82 (1H, d, J=8.0 Hz), 8.15 (1H, s); $^{13}$C NMR (CDCl$_3$, 125 MHz) δ 9.3, 14.9, 22.2, 26.9, 28.1, 35.4 (d, J=6.0 Hz), 36.0, 36.6, 43.2, 45.5, 58.5, 72.4, 72.6, 73.1, 75.6, 76.1, 76.3, 79.3, 80.4, 81.1, 84.6, 128.3, 130.1, 130.4, 130.9, 133.3, 133.7, 134.8, 142.6, 154.8, 156.1, 165.7, 171.1, 205.5; $^{19}$F NMR, (CDCl$_3$, 282 MHz) δ −84.16 (1F, dd, J=23.9, 34.9 Hz), −86.17 (1F, d, J=36.7 Hz); HRMS (FAB+, m/z): Calcd. for C$_{42}$H$_{53}$ClF$_2$N$_2$O$_{15}$.H$^+$, 899.3175; Found 899.3151.

Example 20

3'-Dephenyl-3'-(2,2-difluorovinyl)-2-debenzoyl-2-(3-chlorobenzoyl)-10-methoxycarbonyldocetaxel, SB-T-12855-4 (III-51o)

Yield 70%; white solid; [α]$_D^{20}$ −72.09 (c 4.3, CHCl$_3$); $^1$H NMR (CDCl$_3$, 500 MHz): δ 1.16 (3H, s, H-16), 1.26 (3H, m, H-17), 1.32 (9H, s, Boc), 1.63 (1H, bs, OH), 1.71 (3H, s, H-19), 1.91 (1H, m, H-6b), 1.94 (3H, s, H-18), 2.33 (2H, d, J=9.0 Hz, H-14), 2.42 (3H, s, 4-OAc), 2.46 (1H, d, J=4.0 Hz, OH), 2.59 (1H, ddd, J=7.5, 10.0, 15.5 Hz, H-6a), 3.46 (1H, J=6.0 Hz, OH), 3.81 (1H, d, J=7.0 Hz, H-3), 3.87 (3H, s, H-10-MeO), 4.17 (1H, d, J=8.5 Hz, H-20b), 4.29 (1H, d, J=5.5 Hz, H-2'), 4.32 (1H, d, J=8.5 Hz, H-20a), 4.39 (1H, m, H-7), 4.59 (1H, dd, J=8.0, 24.5 Hz, H-3' vinyl), 4.89 (2H, m, H-3', NH-3'), 5.00 (1H, d, J=8.5 Hz, H-5), 5.64 (1H, d, J=7.5 Hz, H-2), 6.13 (1H, s, H-10), 6.23 (2H, t, J=8.5 Hz, H-13), 7.49 (1H, t, J=8.0 Hz), 7.60 (1H, d, J=7.5 Hz,), 8.01 (1H, d, J=8.0 Hz), 8.14 (1H, s); $^{13}$C NMR (CDCl$_3$, 125 MHz) δ 9.4, 14.9, 21.7, 22.2, 26.6, 28.1, 35.3, 35.6, 43.1, 45.6, 55.6, 58.5, 72.1, 72.5, 73.2, 75.4, 76.3, 78.2, 79.2, 80.5, 80.9, 84.4, 128.3, 130.1, 130.3, 130.9, 132.6, 133.7, 134.9, 143.1, 154.9, 155.7, 165.7, 170.2, 203.8; $^{19}$F NMR (CDCl$_3$, 282 MHz) 8-84.16 (1F, dd, J=23.7, 34.7 Hz), −86.17 (1F, dd, J=34.9 Hz); HRMS (FAB$^+$, m/z): Calcd. for C$_{41}$H$_{50}$ClF$_2$NO$_{16}$.H$^+$, 886.2859; Found 886.2845.

Example 21

3'-Dephenyl-3'-(2,2-difluorovinyl)-2-debenzoyl-2-(3-methoxybenzoyl)-10-acetyldocetaxel, SB-T-12851-1 (III-51p)

Yield 76%; white solid; [α]$_D^{20}$ −74.42 (c 2.15, CHCl$_3$); $^1$H NMR (CDCl$_3$, 400 MHz): δ 1.15 (3H, s, C-16), 1.26 (3H, m, C-17), 1.30 (9H, s, Boc), 1.68 (3H, s, H-19), 1.76 (1H, s, OH), 1.88 (4H, m, H-6b, H-18), 2.24 (3H, s, 10-OAc), 2.33 (2H, m, H-14), 2.38 (3H, s, 4-OAc), 2.49 (1H, d, J=3.5 Hz, OH), 2.56 (1H, ddd, J=6.5, 9.5, 15.0 Hz, H-6a), 3.47 (1H, J=4.5 Hz, OH), 3.81 (1H, d, J=7.5 Hz, H-3), 3.90 (3H, s, 2-m-MeO), 4.15 (1H, d, J=8.0 Hz, H-20b), 4.27 (1H, s, H-2'), 4.36 (1H, d, J=8.0 Hz, H-20a), 4.41 (1H, dd, J=6.0, 10.5 Hz, H-7), 4.58 (1H, ddd, J=1.0, 9.5, 24.5 Hz, H-3'vinyl), 4.87-4.93 (2H, m, H-3', NH-3'), 4.97 (1H, dd, J=2.0, 9.0, H-5), 5.67 (1H, d, J=7.5 Hz, H-2), 6.24 (1H, t, J=8.5 Hz, H-13), 6.30 (1H, s, H-10), 7.15 (1H, dd, J=2.0, 8.0 Hz), 7.40 (1H, t, J=7.5 Hz), 7.45 (1H, s), 7.72 (1H, d, J=8.0 Hz); $^{13}$C NMR (CDCl$_3$, 100 MHz) δ 9.5, 14.8, 20.8, 21.8, 22.3, 26.7, 28.1, 35.5 (d, J=12.2 Hz), 43.2, 45.6, 55.3, 58.5, 72.1, 72.7, 73.1, 75.1, 75.5, 76.4, 77.2, 79.0, 80.5, 81.2, 84.4, 114.0, 120.7, 122.7, 129.7, 130.3, 133.1, 142.1, 154.8, 159.7, 166.9, 170.2, 171.2, 203.5; $^{19}$F NMR (CDCl$_3$, 282 MHz) δ −84.55 (1F, dd, J=33.8, 36.4 Hz), −86.24 (1F, dd, J=36.4 Hz); HRMS (FAB$^+$, m/z): Calcd. for C$_{42}$H$_{53}$F$_2$NO$_{16}$.H$^+$, 866.3405.
Found, 866.3439.

Example 22

3'-Dephenyl-3'-(2,2-difluorovinyl)-2-debenzoyl-2-(3-methoxybenzoyl)-10-cyclopropanecarbonyldocetaxel, SB-T-12852-1 (III-51q)

Yield 99%; white solid; $[\alpha]_D^{20}$ −77.03 (c 5.79, CHCl$_3$); $^1$H NMR (CDCl$_3$, 500 MHz): δ 0.99 (2H, m, CH$_2$-c-Pr), 1.10 (2H, m, CH$_2$-c-Pr), 1.15 (3H, s, C-16), 1.25 (3H, m, C-17), 1.28 (9H, s, Boc), 1.66 (3H, s, H-19), 1.74-1.81 (2H, m, CH-c-Pr, OH), 1.83-1.89 (1H, m, H-6b), 1.87 (3H, s, H-18), 2.31 (2H, m, H-14), 2.37 (3H, s, 4-OAc), 2.53 (1H, ddd, J=6.5, 9.5, 15.0 Hz, H-6a), 2.59 (1H, d, J=3.5 Hz, OH), 3.55 (1H, bs, OH), 3.79 (1H, d, J=7.5 Hz, H-3), 3.88 (3H, s, m-MeO-H2), 4.16 (1H, d, J=8.5 Hz, H-20b), 4.26 (1H, d, J=2.5 Hz, H-2'), 4.34 (1H, d, J=8.5 Hz, H-20a), 4.40 (1H, m, H-7), 4.57 (1H, dd, J=10.0, 24.5 Hz, H-3' vinyl), 4.86 (1H, t, J=8.5 Hz, H-3'), 4.96 (2 H, m, H-5, NH'), 5.65 (1H, d, J=7.0 Hz, H-7), 6.23 (1H, t, J=9.0 Hz, H-13), 6.28 (1H, s, H-10), 7.13 (1H, ddd, J=2.0, 3.0, 8.0 Hz), 7.38 (2H, t, J=7.5 Hz), 7.63 (1H, s), 7.79 (1H, d, J=7.5 Hz); $^{13}$C NMR (CDCl$_3$, 125 MHz) δ 9.2, 9.4, 9.5, 13.0, 14.8, 22.0, 22.3 (d, J=2.9 Hz), 26.7, 28.1, 35.5, (d, J=4.3 Hz), 43.2, 45.6, 55.3, 58.5, 72.1, 72.6, 73.1, 75.1, 75.3, 76.4, 77.2, 79.0, 80.4, 81.0, 84.4, 114.0, 120.6, 122.7, 129.7, 130.3, 133.2, 142.1, 154.8, 156.4, 159.7, 166.9, 170.2, 172.4, 175.1, 203.8; $^{19}$F NMR (CDCl$_3$, 282 MHz) δ −84.62 (1F, dd, J=25.7, 36.7 Hz), −86.29 (1F, d, J=36.4 Hz); HRMS (FAB$^+$, m/z): Calcd. for C$_{44}$H$_{55}$F$_2$NO$_{16}$·H$^+$, 892.3562; Found, 892.3599.

Example 23

3'-Dephenyl-3'-(2,2-difluorovinyl)-2-debenzoyl-2-(3-methoxybenzoyl)-10-propanoyldocetaxel. SB-T-12853-1 (III-51r)

Yield 58%; white solid; $[\alpha]_D^{20}$ −79.78 (c 3.66, CHCl$_3$); $^1$H NMR (CDCl$_3$, 500 MHz): δ 1.15 (3H, s, H-16), 1.22-1.25 (6H, m, H-17, H-10-CH$_3$), 1.30 (9H, s, Boc), 1.67 (3H, s, H-19), 1.71 (1H, s, OH), 1.79 (1H, s, OH), 1.86-1.91 (4H, m, H-6b, H-18), 2.32 (2H, m, H-14), 2.38 (3H, s, 4-OAc), 2.38-2.59 (3H, m, H-6a, H-10, CH$_2$), 3.52 (1H, bs, OH), 3.82 (1H, d, J=7.0 Hz, H-3), 3.89 (H, m-MeO-H2), 4.18 (2H, d, J=8.5 Hz, H-20b), 4.27 (1H, H-2'), 4.35 (1H, d, J=8.5 Hz, H-20a), 4.40 (1H, dd, J=6.5, 11.0 Hz, H-7), 4.58 (1H, ddd, J=1.5, 10.0, 25.0 Hz, H-3'), 4.87 (1H, t, J=9.0 Hz, H-3'), 4.96 (2H, m, NH'-3', H-5), 5.66 (1H, d, J=6.5 Hz, H-2), 6.24 (1H, t, J=9.0 Hz, H-13), 6.31 (1H, s, H-10), 7.15 (1H, ddd, J=1.0, 2.5, 8.5 Hz), 7.39 (1H, t, J=7.5 Hz), 7.65 (1H, s), 7.71 (1H, d, J=8.0 Hz); $^{13}$C NMR (CDCl$_3$, 125 MHz) δ 9.0, 9.5, 14.8, 21.9, 22.3, 26.7, 27.5, 28.1, 35.4 (d, J=15.9 Hz), 43.2, 45.6, 55.3, 58.3, 72.1, 72.6, 73.1, 75.1, 75.3, 76.4, 77.2, 79.0, 81.1, 84.4, 114.0, 122.7, 129.7, 130.3, 133.2, 141.9, 154.8, 159.7, 166.9, 170.2, 174.6, 203.7; $^{19}$F NMR, (CDCl$_3$, 282 MHz) δ −84.58 (1F, dd, J=25.7, 36.7 Hz), −86.26 (1F, d, J=36.7 Hz); HRMS (FAB$^+$, m/z): Calcd. for C$_{43}$H$_{55}$F$_2$NO$_{16}$·H$^+$, 880.3562; Found 880.3578.

Example 24

3'-dephenyl-3'-(2,2-difluorovinyl)-2-debenzoyl-2-(3-methoxybenzoyl)-10-dimethylcarbamate-docetaxel, ST-T-12854-1 (III-51s)

Yield 74%; white solid; $^1$H NMR (CDCl$_3$, 500 MHz): δ 1.15 (3H, s, H-16), 1.25 (3H, s, H-17), 1.29 (9H, s, Boc), 1.67 (3H, s, H-19), 1.76 (1H, bs, OH), 1.88 (1H, m, H-6b), 1.89 (3H, s, H-18), 2.31 (2H, m, H-14), 2.38 (3H, s, 4-OAc), 2.53 (1H, ddd, J=6.5, 10.0, 15.0 Hz, H-6a), 2.96 (3H, s, N-Me), 3.04 (3H, s, N-Me), 3.52 (1H, bs, OH), 3.81 (1H, d, J=7.0 Hz, H-3), 3.90 (3H, s, m-MeO-H2), 4.17 (1H, d, J=8.0 Hz, H-20b), 4.27 (1H, s, H-2'), 4.35 (1H, d, J=8.0 Hz, H-20a), 4.45 (1H, dd, J=6.0, 10.5 Hz, H-7), 4.58 (1H, ddd, J=1.5, 10.0, 25.0 Hz, H-3' vinyl), 4.87 (1H, t, J=8.5 Hz, H-3'), 4.97 (1H, m, H-5, NH-3'), 5.65 (1H, d, J=7.0 Hz, H-2), 6.25 (2H, m, H-10, H-13), 7.14 (1H, dd, J=1.5, 7.5 Hz), 7.39 (2H, t, J=8.0 Hz), 7.65 (1H, s), 7.71 (1H, d, J=7.5 Hz); $^{13}$C NMR (CD+Cl$_3$, 125 MHz) δ 9.3, 14.9, 22.3, 26.9, 28.1, 35.4 (d, J=12.9 Hz), 36.0, 36.6, 43.2, 45.5, 55.3, 58.5, 72.4, 72.7, 73.1, 75.2, 76.1, 76.4, 79.2, 80.4, 81.2, 84.6, 114.0, 120.7, 122.7, 129.7, 130.3, 133.5, 133.7, 142.4, 154.8, 156.1, 159.7, 166.9, 170.1, 205.6; $^{19}$F NMR (CDCl$_3$, 282 MHz) δ −84.60 (1F, dd, J=23.9, 34.9 Hz), −86.30 (1F, d, J=36.4 Hz); HRMS (FAB$^+$, m/z): Calcd. For C$_{43}$H$_{56}$F$_2$N$_2$O$_{16}$·H$^+$, 895.3671; Found 895.3676.

Example 25

3'-Dephenyl-3'-(2,2-difluorovinyl)-2-debenzoyl-2-(3-methoxybenzoyl)-10-methoxycarbonyldocetaxel, SB-T-12855-1 (III-51t)

Yield 89%; white solid; $[\alpha]_D^{20}$ −68.98 (c 4.61, CHCl$_3$); $^1$H NMR (CDCl$_3$, 500 MHz): δ 1.15 (3H, s, H-16), 1.24 (3H, m, H-17), 1.29 (9H, s, Boc), 1.69 (3H, s, H-19), 1.78 (1H, bs, OH), 1.88 (1H, m, H-6b), 1.91 (3H, s, H-18), 2.32 (2H, m, H-14), 2.38 (3H, s, 4-OAc), 2.49 (1H, d, J=4.5 Hz, OH), 2.56 (1H, ddd, J=7.0, 9.5, 15.0 Hz, H-6a), 3.53 (1H, J=5.5 Hz, OH), 3.78 (1H, d, J=6.5 Hz, H-3), 3.87 (3H, s, H-10-MeO), 3.89 (3H, s, m-MeO-H2), 4.18 (1H, d, J=8.5 Hz, H-20b), 4.27 (1H, d, J=3.0 Hz, H-2'), 4.36 (1H, d, J=8.5 Hz, H-20a), 4.41 (1H, m, H-7), 4.59 (1H, dd, J=9.5, 24.5 Hz, H-3' vinyl), 4.86 (1H, t, J=9.0 Hz, H-3'), 4.95 (2H, m, H-5, NH-3'), 5.66 (1H, d, J=7.5 Hz, H-2), 6.12 (1H, s, H-10), 6.24 (1H, t, J=8.5 Hz, H-13), 7.15 (1H, d, J=2.0, 7.5 Hz), 7.39 (1H, t, J=8.0 Hz), 7.64 (1H, s), 7.71 (1H, d, J=7.0 Hz); $^{13}$C NMR (CDCl$_3$, 125 MHz) δ 9.5, 14.9, 21.8, 22.3, 26.6, 28.1, 35.3 (d, J=22.0 Hz), 43.1, 45.6, 55.6, 55.6, 58.5, 72.0, 72.6, 73.1, 75.0, 77.2, 78.2, 79.0, 80.5, 81.1, 84.4, 114.0, 120.7, 129.7, 130.3, 132.8, 142.9, 154.8, 155.7, 159.7, 166.9, 170.3, 203.9; $^{19}$F NMR (CDCl$_3$, 282 MHz) δ −84.60 (1F, dd, J=25.7, 36.7 Hz), −86.27 (1F, dd, J=36.7 Hz); HRMS (FAB$^+$, m/z): Calcd. for C$_{42}$H$_{53}$F$_2$NO$_{17}$·H$^+$, 882.3354; Found 882.3353.

Example 26

3'-Dephenyl-3'-(2,2-difluorovinyl)-2-debenzoyl-2-(3-azidobenzoyl)-10-acetyldocetaxel, SB-T-12851-3 (III-51u)

Yield 49%; white solid; $[\alpha]_D^{20}$ −70.59 (c 3.23, CHCl$_3$); $^1$HNMR (CDCl$_3$, 400 MHz): δ 1.15 (3H, s, C-16), 1.26 (3H, s, C-17), 1.30 (9H, s, Boc), 1.67 (3H, s, H-19), 1.69 (1H, bs, OH), 1.88 (4H, m, H-6b, H-18), 2.24 (3H, s, 10-OAc), 2.32 (2H, m, H-14), 2.39 (3H, s, 4-OAc), 2.49 (1H, bs, OH), 2.56 (1H, ddd, J=7.0, 9.5, 15.0 Hz, H-6a), 3.48 (1H, J=4.0 Hz, OH), 3.82 (1H, d, J=7.0 Hz, H-3), 4.16 (1H, d, J=8.5 Hz, H-20b); 4.26 (1H, s, H-2'), 4.33 (1H, d, J=8.5 Hz, H-20a), 4.42 (1H, dd, J=6.5, 10.5 Hz, H-7), 4.57 (1H, ddd, J=1.5, 9.5, 25.0 Hz, H-3' vinyl), 4.85 (1H, t, J=8.5 Hz, H-3'), 4.93 (1H, d, J=9.5 Hz, NH-3'), 4.98 (1H, d, J=7.5, 1'-5), 5.66 (1H, d, J=7.5 Hz, H-2), 6.22 (1H, t, J=9.0 Hz, H-13), 6.29 (1H, s, H-10), 7.23 (1H, dd, J=1.5, 8.0 Hz), 7.48 (1H, t, J=8.0 Hz), 7.81 (1H, s), 7.89 (1H, d, J=8.0 Hz); $^{13}$C NMR (CDCl$_3$, 100 MHz) δ 9.5, 14.9, 20.8, 21.9, 22.4, 26.7, 28.1, 35.5 (d, J=15.1 Hz), 43.2, 45.6, 58.5, 72.1, 72.6, 73.1, 75.4, 75.5, 76.4, 79.1, 80.4, 81.0, 84.4, 120.1, 124.4, 126.7, 130.2, 133.0, 140.9, 142.2, 154.8, 166.1, 170.3, 171.2, 203.6; $^{19}$F NMR, (CDCl$_3$, 282 MHz) δ −83.99 (1F, dd, J=25.7, 36.7 Hz), −86.12 (1F, d, J=35.0 Hz); HRMS (FAB$^+$, m/z): Calcd. for C$_{41}$H$_{50}$F$_2$N$_4$O$_{15}$.H$^+$, 877.3314; Found, 877.3351.

Example 27

3'-Dephenyl-3'-(2,2-difluorovinyl)-2-debenzoyl-2-(3-azidobenzoyl)-10-cyclopropanecarbonyldocetaxel, SB-T-12852-3 (III-51w)

Yield 78%; white solid; [α]$_D^{20}$ −67.39 (c 5.09, CHCl$_3$); $^1$H NMR(CDCl$_3$, 400 MHz): δ 1.02 (2H, m, CH$_2$-c-Pr), 1.15 (2H, m, CH$_2$-c-Pr), 1.17 (3H, s, C-16), 1.28 (3H, m, C-17), 1.32 (9H, s, Boc), 1.68 (3H, s, H-19), 1.76 (1H, bs, OH), 1.79 (1H, m, CH-c-Pr), 1.86-1.91 (1H, m, H-6b), 1.90 (3H, s, H-18), 2.34 (2H, m, H-14), 2.41 (3H, s, 4-OAc), 2.56 (1H, ddd, J=6.5, 9.5, 15.0 Hz, H-6a), 2.62 (1H, bs, OH), 3.54 (1H, d, J=5.5 Hz, OH), 3.83 (1H, d, J=7.5 Hz, H-3), 4.18 (1H, d, J=8.5 Hz, H-20b), 4.28 (1H, d, 3.0 Hz, H-2'), 4.35 (1H, d, J=8.5 Hz, H-20a), 4.43 (1H, dd, J=6.5, 10.0 Hz, H-7), 4.58 (1H, ddd, J=1.5, 9.0, 24.5 Hz, H-3' vinyl), 4.87 (1H, t, J=8.5 Hz, H-3'), 4.98 (2 H, m, H-5, NH-3'), 5.67 (1H, d, J=7.0 Hz, H-7), 6.24 (1H, t, J=8.0 Hz, H-13), 6.31 (1H, s, H-10), 7.25 (1H, dd, J=1.5, 8.0 Hz), 7.49 (2H, t, J=8.0 Hz), 7.82 (1H, s), 7.90 (1H, d, J=8.0 Hz); $^{13}$C NMR (CDCl$_3$, 100 MHz) δ 9.2, 9.4, 9.5, 13.0, 14.9, 22.0, 22.3, 26.7, 28.1, 35.5, (d, J=7.6 Hz), 43.2, 45.6, 58.5, 72.1, 72.6, 73.1, 75.3, 75.5, 76.4, 79.1, 80.4, 81.0, 84.5, 120.1, 124.4, 126.7, 130.2, 130.8, 133.1, 140.9, 142.3, 154.8, 166.1, 170.3, 175.1, 203.7; $^{19}$F NMR (CDCl$_3$, 282 MHz) δ −84.02 (1F, dd, J=25.7, 34.9 Hz), −86.14 (1F, d, J=34.9 Hz); HRMS (FAB$^+$, m/z): Calcd. for C$_{43}$H$_{52}$F$_2$N$_4$O$_{15}$.H$^+$, 903.3470; Found, 903.3469.

Example 28

3'-Dephenyl-3'-(2,2-difluorovinyl)-2-debenzoyl-2-(3-azidobenzoyl)-10-propanoyldocetaxel, SB-T-12853-3 (III-51x)

Yield 93%; white solid; [α]$_D^{20}$ −67.77 (c 3.32, CHCl$_3$); $^1$H NMR (CDCl$_3$, 500 MHz): δ 1.14 (3H, s, H-16), 1.22-1.25 (6H, m, H-17, H-10-CH$_3$), 1.30 (9H, s, Boc), 1.67 (3H, s, H-19), 1.71 (1H, s, OH), 1.69 (1H, s, OH), 1.85-1.91 (4H, m, H-6b, H-18), 2.32 (2H, m, H-14), 2.39 (3H, s, 4-OAc), 2.47-2.59 (3H, m, H-6a, H-10, CH$_2$), 3.48 (1H, d, J=4.5 Hz, OH), 3.82 (1H, d, J=7.5 Hz, H-3), 4.16 (1H, d, J=8.5 Hz, H-20b), 4.26 (1H, H-2'), 4.33 (1H, d, J=8.5 Hz, H-20a), 4.43 (1H, dd, J=7.0, 11.0 Hz, H-7), 4.56 (1H, ddd, J=1.5, 9.0, 24.5 Hz, H-3'), 4.86 (1H, t, J=8.0 Hz, H-3'), 4.92 (1H, d, J=9.5 Hz, NH'-3'), 4.98 (1H, d, J=8.0 Hz, H-5), 5.66 (1H, d, J=7.5 Hz, H-2), 6.22 (1 H, t, J=8.0 Hz, H-13), 6.31 (1H, s, H-10), 7.23 (1H, dd, J=1.5, 7.5 Hz), 7.48 (1H, t, J=7.5 Hz), 7.81 (1H, s), 7.89 (1H, d, J=8.0 Hz); $^{13}$C NMR (CDCl$_3$, 125 MHz) δ 9.0, 9.5, 14.9, 21.7, 22.4, 26.7, 27.5, 28.1, 35.5 (d, J=11.5 Hz), 43.2, 45.6, 58.5, 72.1, 72.6, 73.1, 75.3, 75.4, 76.4, 79.1, 81.0, 84.5, 120.1, 124.4, 126.7, 130.2, 130.8, 133.2, 140.9, 154.8, 159.7, 166.1, 170.3, 174.6, 203.7; $^{19}$F NMR (CDCl$_3$, 282 MHz) δ −83.99 (1F, dd, J=25.7, 34.7 Hz), −86.12 (1F, d, J=36.7 Hz); FIRMS (FAB$^+$, m/z): Calcd. for C$_{42}$H$_{52}$F$_2$N$_4$O$_{15}$.H$^+$, 891.3470; Found 891.3473.

Example 29

3'-Dephenyl-3'-(2,2-difluorovinyl)-2-debenzoyl-2-(3-azidobenzoyl)-10-dimethylcarbamoyldocetaxel, SB-T-12854-3 (III-51y)

Yield 79%; white solid; [α]$_D^{20}$ −75.39 (c 4.51, CHCl$_3$); $^1$H NMR (CDCl$_3$, 500 MHz): δ 1.15 (3H, s, H-16), 1.25 (3H, s, H-17), 1.30 (9H, s, Boc), 1.66 (3H, s, H-19), 1.75 (1H, bs, OH), 1.87 (1H, m, H-6b), 1.90 (3H, s, H-18), 2.31 (2H, m, H-14), 2.39 (3H, s, 4-OAc), 2.54 (1H, ddd, J=7.0, 10.0, 15.5 Hz, H-6a), 2.96 (3H, s, N-Me), 3.04 (3H, s, N-Me), 3.56 (1H, bs, OH), 3.81 (1H, d, J=7.0 Hz, H-3), 4.16 (1H, d, J=8.5 Hz, H-20b), 4.27 (1H, s, H-2'), 4.32 (1H, d, J=8.5 Hz, H-20a), 4.45 (1H, dd, J=6.5, 10.5 Hz, H-7), 4.57 (1H, ddd, J=1.0, 9.0, 24.0 Hz, H-3' vinyl), 4.85 (1H, t, J=8.0 Hz, H-3'), 4.97 (2H, m, H-5, NH-3'), 5.65 (1H, d, J=7.0 Hz, H-2), 6.23 (1H, t, J=9.5 Hz, H-13), 6.25 (1H, s, H-10), 7.23 (1H, dd, J=1.5, 8.5 Hz), 7.47 (1H, t, J=8.0 Hz), 7.80 (1H, s), 7.89 (1H, d, J=8.0 Hz); $^{13}$C NMR (CDCl$_3$, 125 MHz) δ 9.3, 14.9, 22.3, 26.9, 28.1, 35.4 (d, J=6.6 Hz), 36.0, 36.6, 43.2, 58.5, 72.4, 72.6, 73.1, 75.6, 76.1, 76.3, 79.2, 80.1, 84.7, 120.7, 120.2, 124.3, 126.7, 130.2, 130.9, 133.4, 140.9, 142.6, 154.9, 156.1, 166.1, 170.3, 205.5; $^{19}$F NMR (CDCl$_3$, 282 MHz) δ −84.06 (1F, dd, J=25.7, 34.7 Hz), −86.17 (1F, d, J=36.7 Hz); HRMS (FAB$^+$, m/z): Calcd. for C$_{42}$H$_{53}$F$_2$N$_5$O$_{15}$.H$^+$, 906.3579; Found 906.3588.

Example 30

3'-Dephenyl-3'-(2,2-difluorovinyl)-2-debenzoyl-2-(3-azidobenzoyl)-10-methoxycarbonyldocetaxel, SB-T-12855-3 (III-51z)

Yield 77%; white solid; [α]$_D^{20}$ −66.67 (c 3.9, CHCl$_3$); $^1$H NMR (CDCl$_3$, 400 MHz): δ 1.15 (3H, s, H-16), 1.24 (3H, s, H-17), 1.29 (9H, s, Boc), 1.69 (3H, s, H-19), 1.71 (1H, bs, OH), 1.89 (1H, m, H-6b), 1.92 (3H, s, H-18), 2.32 (2H, m, H-14), 2.39 (3H, s, 4-OAc), 2.49 (1H, bs, OH), 2.56 (1H, ddd, J=6.5, 9.5, 14.5 Hz, H-6a), 3.51 (1H, bs, OH), 3.79 (1H, d, J=7.0 Hz, H-3), 3.87 (3H, s, H-10-MeO), 4.17 (1H, d, J=8.5 Hz, H-20b), 4.26 (1H, s, H-2'), 4.33 (1H, d, J=8.5 Hz, H-20a), 4.40 (1H, dd, J=7.0, 11.0 Hz, H-7), 4.57 (1H, ddd, J=1.0, 9.0, 24.5 Hz, H-3' vinyl), 4.85 (1H, t, J=8.5 Hz, H-3'), 4.96 (2H, m, H-5, NH-3'), 5.66 (1H, d, J=7.5 Hz, H-2), 6.12 (1H, s, H-10), 6.22 (1H, t, J=9.0 Hz, H-13), 7.23 (1H, dd, J=1.5, 6.5 Hz), 7.48 (1H, t, J=7.5 Hz), 7.81 (1H, s), 7.89 (1H, d, J=8.0 Hz); $^{13}$C NMR (CDCl$_3$, 100 MHz) δ 9.5, 14.9, 21.8, 22.4, 26.6, 28.1, 35.4 (d, J=18.6 Hz), 43.1, 45.6, 55.6, 55.6, 58.5, 72.0, 72.5, 73.1, 75.4, 76.3, 78.2, 79.1, 80.4, 81.0, 84.3, 120.1, 124.4, 126.7, 130.2, 130.8, 132.7, 140.9, 143.0, 154.7, 155.7, 166.1, 170.4, 203.8; $^{19}$F NMR (CDCl$_3$, 282 MHz) δ −84.01 (1F, dd, J=25.7, 36.7 Hz), −86.13 (1F, d, J=36.7 Hz); HRMS (FAB$^+$, m/z): Calcd. for C$_{41}$H$_{50}$F$_2$N$_4$O$_{16}$.H$^+$, 893.3263; Found 893.3269.

Example 31

Tumor Growth Inhibitory Activity of Fluorotaxoids

Fluorotaxoids were evaluated in their tumor growth inhibitory activities against human tumor cell lines, MCF7 (mammary carcinoma) or MCF7-R (mammary carcinoma cells 250-fold resistant to paclitaxel), after 72 h drug exposure according to literature methods. Results are shown for some selected compounds in the tables below.

In the tables, lower numbers indicate higher potency (or greater activity). Paclitaxel was used as the standard for comparison. The data represent the mean values of at least three separate experiments.

Cytotoxicity (IC$_{50}$ nM) of CF$_2$=CH-Taxoids (1)

| CF$_2$=CH-Taxoid | R | X | MCF7 (breast) | MCF7-R (breast) | R/S |
|---|---|---|---|---|---|
| Paclitaxel | Me | H | 1.2 | 300 | 250 |
| SB-T-12851 | Me | H | 0.099 | 0.95 | 9.6 |
| SB-T-12852 | cyclo-Pr | H | 0.12 | 6.03 | 53 |
| SB-T-12853 | Et | H | 0.12 | 1.2 | 10 |
| SB-T-12854 | Me$_2$N | H | 0.13 | 4.27 | 33 |
| SB-T-12855 | MeO | H | 0.14 | 1.29 | 9.2 |

Cytotoxicity (IC$_{50}$ nM) of CF$_2$=CH-Taxoids (2)

| CF$_2$=CH-Taxoid | R | X | MCF7 (breast) | MCF7-R (breast) | R/S |
|---|---|---|---|---|---|
| Paclitaxel | Me | H | 1.2 | 300 | 250 |
| SB-T-12851-1 | Me | MeO | 0.25 | 1.5 | 6.0 |
| SB-T-12852-1 | cyclo-Pr | MeO | 0.092 | 0.48 | 5.2 |
| SB-T-12853-1 | Et | MeO | 0.34 | 0.57 | 1.7 |
| SB-T-12854-1 | Me$_2$N | MeO | 0.11 | 0.96 | 8.7 |
| SB-T-12855-1 | MeO | MeO | 0.078 | 0.50 | 6.4 |

Cytotoxicity (IC$_{50}$ nM) of CF$_2$=CH-Taxoids (3)

| CF$_2$=CH-Taxoid | R | X | MCF7 (breast) | MCF7-R (breast) | R/S |
|---|---|---|---|---|---|
| Paclitaxel | Me | H | 1.2 | 300 | 250 |
| SB-T-12851-2 | Me | F | 0.13 | 1.53 | 12 |
| SB-T-12852-2 | cyclo-Pr | F | 0.076 | 1.72 | 23 |
| SB-T-12853-2 | Et | F | 0.23 | 2.54 | 11 |
| SB-T-12854-2 | Me$_2$N | F | 0.17 | 2.25 | 9.4 |
| SB-T-12855-2 | MeO | F | 0.12 | 1.85 | 11 |

Cytotoxicity (IC$_{50}$ nM) of CF$_2$=CH-Taxoids (4)

| CF$_2$=CH-Taxoid | R | X | MCF7 (breast) | MCF7-R (breast) | R/S |
|---|---|---|---|---|---|
| Paclitaxel | Me | H | 1.2 | 300 | 250 |
| SB-T-12851-3 | Me | N$_3$ | 0.092 | 0.34 | 3.7 |
| SB-T-12852-3 | cyclo-Pr | N$_3$ | 0.092 | 0.45 | 4.9 |
| SB-T-12853-3 | Et | N$_3$ | 0.13 | 0.38 | 2.9 |
| SB-T-12854-3 | Me$_2$N | N$_3$ | 0.13 | 0.45 | 3.7 |
| SB-T-12855-3 | MeO | N$_3$ | 0.076 | 0.40 | 5.3 |

Cytotoxicity (IC$_{50}$ nM) of CF$_2$=CH-Taxoids (5)

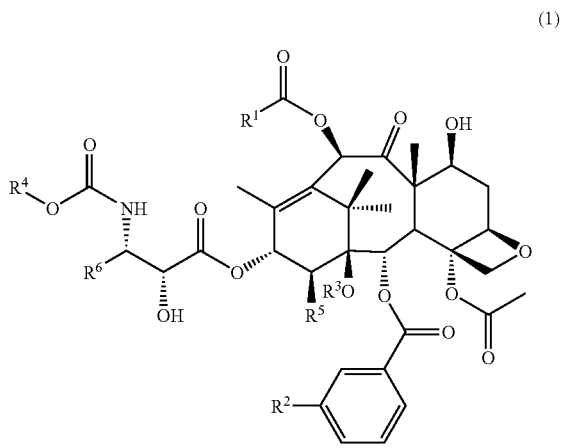

| CF$_2$=CH-Taxoid | R | X | MCF7 (breast) | MCF7-R (breast) | R/S |
|---|---|---|---|---|---|
| Paclitaxel | Me | H | 1.2 | 300 | 250 |
| SB-T-12851-4 | Me | Cl | 0.13 | 0.70 | 5.4 |
| SB-T-12852-4 | cyclo-Pr | Cl | 0.12 | 0.50 | 4.2 |
| SB-T-12853-4 | Et | Cl | 0.13 | 0.45 | 3.5 |
| SB-T-12854-4 | Me$_2$N | Cl | 0.93 | 2.6 | 2.8 |
| SB-T-12855-4 | MeO | Cl | 0.099 | 1.15 | 12 |

Assessment of cell growth inhibition was determined according to the methods of Skehan et al (See Skehan et al., J. Nat. Cancer Inst., 82, 1107 (1990)). Briefly, cells were plated between 400 and 1200 cells/well in 96 well plates and incubated at 37° C. for 15-18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 h incubation, 100 μL of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 μL) was added to each well. Following a 5 minute incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

Data were fit with the Sigmoid-Emax concentration-effect model with non-linear regression, weighted by the reciprocal of the square of the predicted response (see Holford, N. H. G.; Scheiner, L. B., "Understanding the dose-effect relationship: Clinical applications of pharmaco-kinetic-pharmacodynamic models," *Clin. Pharmacokin.*, 6, 429-453 (1981)). The fitting software was developed by the Roswell Park Cancer Institute with Microsoft FORTRAN, and uses the Marquardt algorithm (see Marquardt, D. W., "An algorithm for least squares estimation of nonlinear parameters," *J. Soc. Ind. Appl. Math.*, 11, 431-441 (1963)) as adopted by Nash for the non-linear regression (see Nash, J. C., "Compact numerical method for computers: Linear algebra and function minimization," John Wiley & Sons, New York, 1979). The concentration of drug which resulted in 50% growth inhibition (IC$_{50}$) was calculated.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

We claim:

1. A taxoid compound represented by the formula:

(1)

[Structural formula of taxoid compound with substituents R$^1$, R$^2$, R$^3$, R$^4$, R$^5$, R$^6$]

wherein:
R$^1$ represents an alkyl, alkenyl, alkylamino, dialkylamino, or alkoxy group having one to six carbon atoms; a non-aromatic carbocyclic alkyl or alkenyl group having three to seventeen ring carbon atoms; a carbocyclic aryl group having six to eighteen ring carbon atoms; a non-aromatic heterocyclic group having three to seventeen ring carbon atoms or a heterocyclic aryl group having five to seventeen ring carbon atoms, wherein said cyclic groups can be unfused or fused, and unsubstituted or substituted;

R$^2$ represents a hydrogen; alkyl, alkenyl, alkoxy, alkenyloxy, acyloxy, alkylthio, alkenylthio, alkylamino or dialkylamino having one to six carbon atoms; halogen; fluoroalkyl group having one to three fluorine atoms and one to three carbon atoms; hydroxyl; carboxyl; amino or azido;

R$^3$ and R$^5$ both represent hydrogen, or R$^3$ and R$^5$ are linked as a cyclic carbonate;

R$^4$ represents an alkyl or alkenyl group having one to six carbon atoms; or a cycloalkyl or cycloalkenyl group having three to seven ring carbon atoms; and R$^6$ represents a fluorovinyl, difluorovinyl, or trifluorovinyl group having the formula (2)

wherein R$^7$, R$^8$, and R$^9$ each independently represent a hydrogen or fluoro group,
provided that at least one of R$^7$, R$^8$, and R$^9$ represents a fluoro group.

2. The taxoid compound according to claim 1, wherein R$^7$ represents hydrogen and each of R$^8$ and R$^9$ represents a fluoro group.

3. The taxoid compound according to claim 1, wherein R$^4$ represents tert-butyl.

4. The taxoid compound according to claim 3, represented by the formula:

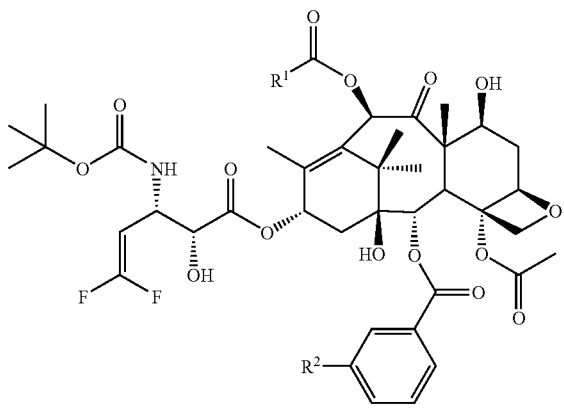

(3)

wherein R¹ represents an alkyl, alkenyl, alkylamino, dialkylamino, or alkoxy group having one to six carbon atoms; a non-aromatic carbocyclic alkyl or alkenyl group having three to seventeen ring carbon atoms; a carbocyclic aryl group having six to eighteen ring carbon atoms; a non-aromatic heterocyclic group having three to seventeen ring carbon atoms or a heterocyclic aryl group having five to seventeen ring carbon atoms, wherein said cyclic groups can be unfused or fused, and unsubstituted or substituted; and wherein $R^2$ represents a hydrogen; alkyl, alkenyl, alkoxy, alkenyloxy, acyloxy, alkylthio, alkenylthio, alkylamino or dialkylamino having one to six carbon atoms; halogen; fluoroalkyl group having one to three fluorine atoms and one to three carbon atoms; hydroxyl; carboxyl; amino or azido.

5. The taxoid compound according to claim 4, wherein $R^1$ represents methyl, ethyl, methoxy, dimethylamino or cyclopropyl and $R^2$ represents hydrogen, methyl, methoxy, chloro, fluoro or azido.

6. The taxoid compound according to claim 4, wherein $R^1$ represents methyl, ethyl, methoxy, dimethylamino or cyclopropyl and $R^2$ represents methoxy.

7. The taxoid compound according to claim 4, wherein $R^1$ represents methyl, ethyl, methoxy, dimethylamino or cyclopropyl and $R^2$ represents azido.

8. The taxoid compound according to claim 4, wherein $R^1$ represents methyl, ethyl, methoxy, dimethylamino or cyclopropyl and $R^2$ represents chloro.

9. The taxoid compound according to claim 4, wherein $R^1$ represents methyl, ethyl, methoxy, dimethylamino or cyclopropyl and $R^2$ represents fluoro.

10. A pharmaceutical composition comprising a taxoid compound according to claim 1 and a pharmaceutically acceptable carrier.

11. A method for inhibiting the growth of cancer cells in a mammal in need thereof, the method comprising administering to the mammal an effective amount of a taxoid compound according to claim 1.

* * * * *

UNITED STATES PATENT AND TRADEMARK OFFICE
CERTIFICATE OF CORRECTION

PATENT NO. : 7,981,926 B2
APPLICATION NO. : 11/990323
DATED : July 19, 2011
INVENTOR(S) : Iwao Ojima Page 1 of 1

It is certified that error appears in the above-identified patent and that said Letters Patent is hereby corrected as shown below:

Col. 1 lines 1-10

Now reads:

The present invention was made with government support under Grant No. R01 GM 42798 awarded by the National Institute of General Medical Sciences and Grant No. RO1 CA10331 awarded by the National Cancer Institute. The United States government has certain rights in this invention.

Should read:

This invention was made with government support under grant numbers CA103314 and GM042798 awarded by the National Institute of Health. The government has certain rights in the invention.

Signed and Sealed this
Twentieth Day of December, 2011

David J. Kappos
*Director of the United States Patent and Trademark Office*